United States Patent
Kudo

(10) Patent No.: US 12,257,145 B2
(45) Date of Patent: Mar. 25, 2025

(54) INTRAOCULAR LENS INJECTOR WITH CONTAINER

(71) Applicant: Hoya Medical Singapore Pte. Ltd., Singapore (SG)

(72) Inventor: Kazunori Kudo, Saku (JP)

(73) Assignee: Hoya Medical Singapore Pte. Ltd., Singapore (SG)

( * ) Notice: Subject to any disclaimer, the term of this patent is extended or adjusted under 35 U.S.C. 154(b) by 1058 days.

(21) Appl. No.: 17/055,186

(22) PCT Filed: Apr. 25, 2019

(86) PCT No.: PCT/JP2019/017744
§ 371 (c)(1),
(2) Date: Nov. 13, 2020

(87) PCT Pub. No.: WO2019/220922
PCT Pub. Date: Nov. 21, 2019

(65) Prior Publication Data
US 2021/0145570 A1    May 20, 2021

(30) Foreign Application Priority Data
May 16, 2018    (JP) .................... 2018-094807

(51) Int. Cl.
*A61F 2/16*    (2006.01)
(52) U.S. Cl.
CPC ............ *A61F 2/167* (2013.01); *A61F 2/1678* (2013.01)
(58) Field of Classification Search
CPC ...... A61F 2/167; A61F 2/1678; A61F 2/1691; A61F 2/1694
See application file for complete search history.

(56) References Cited

U.S. PATENT DOCUMENTS

| | | |
|---|---|---|
| 2,761,446 A | 9/1956 | Reed |
| 3,212,685 A | 10/1965 | Swan |
| (Continued) | | |

FOREIGN PATENT DOCUMENTS

| | | |
|---|---|---|
| CN | 101073519 A | 11/2007 |
| CN | 204601363 U | 9/2015 |
| (Continued) | | |

OTHER PUBLICATIONS

Presentation given by James P. McCulley, titled "Benefits of Newest Generation Fully Preloaded Aspheric IOL Delivery System," on Sep. 16, 2008 at the "Aspheric IOLs" free paper session of the 2008 Congress of the European Society of Cataract and Refractive Surgery, in Berlin, Germany.
(Continued)

*Primary Examiner* — Ashley L Fishback
*Assistant Examiner* — Chima U Igboko
(74) *Attorney, Agent, or Firm* — Henricks Slavin LLP

(57) ABSTRACT

There is provided an intraocular ring injector which allows an operator to stably and normally house the intraocular ring in the intraocular ring injector, which is an intraocular ring injector 20 with a container configured so that an intraocular ring injector 10 is housed in a container 4, for injecting an intraocular ring C into an eye for retaining a shape of a lens capsule, the intraocular ring injector comprising:
a hollow body 1 having a hollow part in which the intraocular ring C is housed;
a plunger 2 that moves through an inside of the hollow body 1 in an axial direction of the hollow body 1; and
a pushing member 3 that pushes out the intraocular ring C by moving together with the plunger 2 through the inside of the hollow body 1 and toward front part of the hollow body 1 in the axial direction, (Continued)

wherein the container 4 has a moving mechanism of moving the hollow body 1 and the plunger 2 relatively in the axial direction, while housing the intraocular ring injector 10 in the container 4.

19 Claims, 11 Drawing Sheets

(56) References Cited

U.S. PATENT DOCUMENTS

| | | |
|---|---|---|
| 4,205,747 A | 6/1980 | Gilliam et al. |
| 4,269,307 A | 5/1981 | LaHaye |
| 4,423,809 A | 1/1984 | Mazzocco |
| 4,573,998 A | 3/1986 | Mazzocco |
| 4,608,049 A | 8/1986 | Kelman |
| 4,634,423 A | 1/1987 | Bailey |
| 4,681,102 A | 7/1987 | Bartell |
| 4,697,697 A | 10/1987 | Graham et al. |
| 4,699,140 A | 10/1987 | Holmes |
| 4,702,244 A | 10/1987 | Mazzocco |
| 4,715,373 A | 12/1987 | Mazzocco et al. |
| 4,747,404 A | 5/1988 | Jampel et al. |
| 4,750,498 A | 6/1988 | Graham |
| 4,759,359 A | 7/1988 | Willis et al. |
| 4,763,650 A | 8/1988 | Hauser |
| 4,765,329 A | 8/1988 | Cumming et al. |
| 4,769,034 A | 9/1988 | Poley |
| 4,781,719 A | 11/1988 | Kelman |
| 4,787,904 A | 11/1988 | Severin |
| 4,810,249 A | 3/1989 | Haber et al. |
| 4,819,631 A | 4/1989 | Poley |
| 4,834,094 A | 5/1989 | Patton |
| 4,836,201 A | 6/1989 | Patton |
| 4,862,885 A | 9/1989 | Cumming |
| 4,880,000 A | 11/1989 | Holmes et al. |
| 4,919,130 A | 4/1990 | Stoy et al. |
| 4,934,363 A | 6/1990 | Smith et al. |
| 4,955,889 A | 9/1990 | Van Gent |
| 4,976,716 A | 12/1990 | Cumming |
| 4,988,352 A | 1/1991 | Poley |
| 4,994,028 A | 2/1991 | Leonard et al. |
| 5,066,297 A | 11/1991 | Cumming |
| 5,098,439 A | 3/1992 | Hill et al. |
| 5,123,905 A | 6/1992 | Kelman |
| 5,139,501 A | 8/1992 | Klaas |
| 5,171,241 A | 12/1992 | Buboltz et al. |
| 5,176,686 A | 1/1993 | Poley |
| 5,178,622 A | 1/1993 | Lehner, II |
| 5,190,552 A | 3/1993 | Kelman |
| 5,190,553 A | 3/1993 | Kanert et al. |
| 5,222,972 A | 6/1993 | Hill et al. |
| 5,242,450 A | 9/1993 | McDonald |
| 5,259,395 A | 11/1993 | Li |
| 5,275,604 A | 1/1994 | Rheinish et al. |
| 5,281,227 A | 1/1994 | Sussman |
| 5,304,182 A | 4/1994 | Rheinish et al. |
| 5,354,333 A | 10/1994 | Kammann et al. |
| 5,395,378 A | 3/1995 | McDonald |
| 5,425,734 A | 6/1995 | Blake |
| 5,454,818 A | 10/1995 | Hambleton et al. |
| 5,468,246 A | 11/1995 | Blake |
| 5,474,562 A | 12/1995 | Orchowski et al. |
| 5,494,484 A | 2/1996 | Feingold |
| 5,496,328 A | 3/1996 | Nakajima et al. |
| 5,499,987 A | 3/1996 | Feingold |
| 5,562,676 A | 10/1996 | Brady et al. |
| 5,571,113 A | 11/1996 | McDonald |
| 5,578,042 A | 11/1996 | Cumming |
| 5,582,613 A | 12/1996 | Brady |
| 5,582,614 A | 12/1996 | Feingold |
| 5,584,304 A | 12/1996 | Brady |
| 5,616,148 A | 4/1997 | Eagles et al. |
| 5,620,450 A | 4/1997 | Eagles et al. |
| 5,643,275 A | 7/1997 | Blake |
| 5,643,276 A | 7/1997 | Zaleski |
| 5,645,534 A | 7/1997 | Chanoch |
| 5,653,715 A | 8/1997 | Reich et al. |
| 5,653,753 A | 8/1997 | Brady et al. |
| 5,702,402 A | 12/1997 | Brady |
| 5,702,441 A | 12/1997 | Zhou |
| 5,716,364 A | 2/1998 | Makker et al. |
| 5,728,075 A | 3/1998 | Levander |
| 5,728,102 A | 3/1998 | Feingold et al. |
| 5,735,858 A | 4/1998 | Makker et al. |
| 5,766,181 A | 6/1998 | Chambers et al. |
| 5,772,666 A | 6/1998 | Feingold et al. |
| 5,772,667 A | 6/1998 | Blake |
| 5,776,138 A | 7/1998 | Vidal et al. |
| 5,800,442 A | 9/1998 | Wolf et al. |
| 5,803,925 A | 9/1998 | Yang et al. |
| 5,807,400 A | 9/1998 | Chambers et al. |
| 5,810,833 A | 9/1998 | Brady et al. |
| 5,810,834 A | 9/1998 | Heyman |
| 5,860,984 A | 1/1999 | Chambers et al. |
| 5,860,986 A | 1/1999 | Reich et al. |
| 5,868,751 A | 2/1999 | Feingold |
| 5,868,752 A | 2/1999 | Makker et al. |
| 5,873,879 A | 2/1999 | Figueroa et al. |
| 5,876,406 A | 3/1999 | Wolf et al. |
| 5,876,407 A | 3/1999 | Makker et al. |
| 5,876,440 A | 3/1999 | Feingold |
| 5,891,152 A | 4/1999 | Feingold |
| 5,902,307 A | 5/1999 | Feingold et al. |
| 5,919,197 A | 7/1999 | McDonald |
| 5,921,989 A | 7/1999 | Deacon et al. |
| 5,928,245 A | 7/1999 | Wolf et al. |
| 5,941,886 A | 8/1999 | Feingold |
| 5,942,277 A | 8/1999 | Makker et al. |
| 5,944,725 A | 8/1999 | Cicenas |
| 5,947,974 A | 9/1999 | Brady et al. |
| 5,947,975 A | 9/1999 | Kikuchi et al. |
| 5,957,748 A | 9/1999 | Ichiha |
| 5,957,896 A | 9/1999 | Bendek et al. |
| 6,001,107 A | 12/1999 | Feingold |
| 6,010,510 A | 1/2000 | Brown et al. |
| 6,022,358 A | 2/2000 | Wolf et al. |
| 6,048,348 A | 4/2000 | Chambers et al. |
| 6,050,999 A | 4/2000 | Paraschac et al. |
| 6,051,000 A | 4/2000 | Heyman |
| 6,056,757 A | 5/2000 | Feingold et al. |
| 6,056,758 A | 5/2000 | Vidal et al. |
| 6,059,791 A | 5/2000 | Chambers |
| 6,074,397 A | 6/2000 | Chambers et al. |
| 6,083,230 A | 7/2000 | Makker et al. |
| 6,093,193 A | 7/2000 | Makker et al. |
| 6,129,733 A | 10/2000 | Brady et al. |
| 6,142,999 A | 11/2000 | Brady et al. |
| 6,143,000 A | 11/2000 | Feingold |
| 6,162,229 A * | 12/2000 | Feingold ............... A61F 2/167 606/107 |
| 6,174,315 B1 | 1/2001 | Chambers et al. |
| 6,214,015 B1 | 4/2001 | Reich et al. |
| 6,241,737 B1 | 6/2001 | Feingold |
| 6,248,111 B1 | 6/2001 | Glick et al. |
| 6,251,114 B1 | 6/2001 | Farmer et al. |
| 6,254,607 B1 | 7/2001 | Makker et al. |
| 6,267,768 B1 | 7/2001 | Deacon |
| 6,283,975 B1 | 9/2001 | Glick et al. |
| 6,283,976 B1 | 9/2001 | Portney |
| 6,312,433 B1 | 11/2001 | Butts |
| 6,334,862 B1 | 1/2002 | Vidal et al. |
| 6,336,932 B1 | 1/2002 | Figueroa et al. |
| 6,355,046 B2 | 3/2002 | Kikuchi et al. |
| 6,371,960 B2 | 4/2002 | Heyman et al. |
| 6,386,357 B1 | 5/2002 | Egawa |
| 6,387,101 B1 | 5/2002 | Butts et al. |
| 6,398,788 B1 | 6/2002 | Makker et al. |
| 6,406,481 B2 | 6/2002 | Feingold et al. |
| 6,428,545 B2 | 8/2002 | Portney |
| 6,447,519 B1 | 9/2002 | Brady et al. |
| 6,447,520 B1 | 9/2002 | Ott et al. |
| 6,468,282 B2 | 10/2002 | Kikuchi et al. |
| 6,471,708 B2 | 10/2002 | Green |

(56) References Cited

U.S. PATENT DOCUMENTS

| | | |
|---|---|---|
| 6,491,697 B1 | 12/2002 | Clark et al. |
| 6,497,708 B1 | 12/2002 | Cumming |
| 6,500,181 B1 | 12/2002 | Portney |
| 6,503,275 B1 | 1/2003 | Cumming |
| 6,506,195 B2 | 1/2003 | Chambers et al. |
| 6,537,283 B2 | 3/2003 | Van Noy |
| 6,540,754 B2 | 4/2003 | Brady |
| 6,554,839 B2 | 4/2003 | Brady |
| 6,558,395 B2 | 5/2003 | Hjertman et al. |
| 6,605,093 B1 | 8/2003 | Blake |
| 6,607,537 B1 | 8/2003 | Binder |
| 6,629,979 B1 | 10/2003 | Feingold |
| 6,666,871 B2 | 12/2003 | Kikuchi et al. |
| 6,679,891 B2 | 1/2004 | Makker et al. |
| 6,685,740 B2 | 2/2004 | Figueroa et al. |
| 6,712,848 B1 | 3/2004 | Wolf et al. |
| 6,723,104 B2 | 4/2004 | Ott |
| 6,733,507 B2 | 5/2004 | McNicholas et al. |
| 6,749,631 B1 | 6/2004 | Pietrini et al. |
| 6,793,674 B2 | 9/2004 | Zapata |
| 6,858,033 B2 | 2/2005 | Kobayashi |
| 6,921,405 B2 | 7/2005 | Feingold et al. |
| 6,923,815 B2 | 8/2005 | Brady et al. |
| 6,976,989 B1 | 12/2005 | Vincent |
| 7,014,641 B2 | 3/2006 | Kobayashi et al. |
| 7,025,782 B2 | 4/2006 | Kobayashi et al. |
| 7,033,366 B2 | 4/2006 | Brady |
| 7,037,312 B2 | 5/2006 | Kikuchi et al. |
| 7,074,227 B2 | 7/2006 | Portney |
| 7,097,649 B2 | 8/2006 | Meyer |
| 7,131,976 B2 | 11/2006 | Kobayashi et al. |
| 7,156,854 B2 | 1/2007 | Brown et al. |
| 7,348,038 B2 | 3/2008 | Makker et al. |
| 7,422,604 B2 | 9/2008 | Vaquero et al. |
| 7,429,263 B2 | 9/2008 | Vaquero et al. |
| 7,458,976 B2 | 12/2008 | Peterson et al. |
| 7,476,230 B2 | 1/2009 | Ohno et al. |
| 7,494,505 B2 | 2/2009 | Kappelhof et al. |
| 7,645,300 B2 | 1/2010 | Tsai |
| 8,273,122 B2 | 9/2012 | Anderson |
| 8,382,769 B2 | 2/2013 | Inoue |
| 8,460,311 B2 | 6/2013 | Ishii |
| 8,470,032 B2 | 6/2013 | Inoue et al. |
| 8,475,526 B2 | 7/2013 | Pynson |
| 8,475,528 B2 | 7/2013 | Ichinohe et al. |
| 8,523,877 B2 | 9/2013 | Ichinohe et al. |
| 8,523,941 B2 | 9/2013 | Ichinohe et al. |
| 8,535,375 B2 | 9/2013 | Ichinohe et al. |
| 8,545,512 B2 | 10/2013 | Ichinohe et al. |
| 8,574,239 B2 | 11/2013 | Ichinohe et al. |
| 8,603,103 B2 | 12/2013 | Kudo et al. |
| 8,647,382 B2 | 2/2014 | Kudo et al. |
| 8,702,795 B2 | 4/2014 | Shoji et al. |
| 8,747,465 B2 | 6/2014 | Someya et al. |
| 8,968,328 B2 | 3/2015 | Ichinohe et al. |
| 9,114,006 B2 | 8/2015 | Inoue |
| 9,114,007 B2 | 8/2015 | Ichinohe et al. |
| 9,186,246 B2 | 11/2015 | Inoue |
| 9,220,593 B2 | 12/2015 | Ichinohe |
| 9,237,947 B2 | 1/2016 | Valle |
| 9,289,288 B2 | 3/2016 | Someya et al. |
| 9,314,373 B2 | 4/2016 | Kudo et al. |
| 9,326,847 B2 | 5/2016 | Sanger |
| 9,364,320 B2 | 6/2016 | Ichinohe et al. |
| 9,554,894 B2 | 1/2017 | Inoue |
| 9,572,710 B1 | 2/2017 | Kudo et al. |
| 9,655,718 B2 | 5/2017 | Kudo |
| 9,687,340 B2 | 6/2017 | Anderson |
| 9,877,826 B2 | 1/2018 | Kudo et al. |
| 9,901,442 B2 | 2/2018 | Kudo et al. |
| 9,907,647 B2 | 3/2018 | Inoue |
| 9,980,811 B2 | 5/2018 | Kudo et al. |
| 10,039,668 B2 | 8/2018 | Kudo et al. |
| 10,231,826 B2 | 5/2019 | Hangya et al. |
| 10,383,723 B2 | 8/2019 | Kudo |
| 10,390,940 B2 | 8/2019 | Someya et al. |
| 10,405,971 B2 | 9/2019 | Someya et al. |
| 10,517,717 B2 | 12/2019 | Inoue |
| 10,799,339 B2 | 10/2020 | Kudo et al. |
| 10,849,738 B2 | 12/2020 | Kudo et al. |
| 11,033,382 B2 | 6/2021 | Watanabe et al. |
| 11,439,499 B2 | 9/2022 | Wensrich et al. |
| 11,938,019 B2 | 3/2024 | Someya et al. |
| 12,076,231 B2 | 9/2024 | Noda et al. |
| 2001/0007942 A1 | 7/2001 | Kikuchi et al. |
| 2001/0020171 A1 | 9/2001 | Heyman |
| 2002/0103490 A1 | 8/2002 | Brady |
| 2002/0151904 A1 | 10/2002 | Feingold et al. |
| 2002/0165610 A1 | 11/2002 | Waldock |
| 2002/0193805 A1 | 12/2002 | Ott et al. |
| 2003/0036765 A1 | 2/2003 | Van Noy |
| 2003/0040755 A1 | 2/2003 | Meyer |
| 2003/0050646 A1* | 3/2003 | Kikuchi ............... A61F 2/167 606/107 |
| 2003/0050647 A1 | 3/2003 | Brady |
| 2003/0088253 A1 | 5/2003 | Seil |
| 2003/0139749 A1 | 7/2003 | Kikuchi et al. |
| 2003/0181921 A1 | 9/2003 | Jeannin |
| 2003/0195522 A1 | 10/2003 | McNicholas |
| 2003/0212406 A1 | 11/2003 | Kobayashi et al. |
| 2003/0212407 A1 | 11/2003 | Kikuchi |
| 2003/0212408 A1 | 11/2003 | Kobayashi |
| 2003/0212409 A1 | 11/2003 | Kobayashi et al. |
| 2004/0039345 A1 | 2/2004 | Benz et al. |
| 2004/0111094 A1 | 6/2004 | Meyer |
| 2004/0116937 A1* | 6/2004 | Portney ............... A61F 2/1664 606/107 |
| 2004/0117012 A1 | 6/2004 | Vincent |
| 2004/0127911 A1 | 7/2004 | Figueroa |
| 2004/0147938 A1 | 7/2004 | Dusek et al. |
| 2004/0186428 A1 | 9/2004 | Ray |
| 2004/0238392 A1 | 12/2004 | Peterson et al. |
| 2004/0243141 A1 | 12/2004 | Brown et al. |
| 2005/0033308 A1 | 2/2005 | Callahan et al. |
| 2005/0049605 A1 | 3/2005 | Vaquero et al. |
| 2005/0049606 A1 | 3/2005 | Vaquero et al. |
| 2005/0055011 A1 | 3/2005 | Enggaard |
| 2005/0125000 A1 | 6/2005 | Tourrette et al. |
| 2005/0143750 A1 | 6/2005 | Vaquero |
| 2005/0182419 A1 | 8/2005 | Tsai |
| 2005/0222578 A1 | 10/2005 | Vaquero |
| 2005/0261703 A1 | 11/2005 | Feingold et al. |
| 2006/0085013 A1 | 4/2006 | Dusek |
| 2006/0142781 A1 | 6/2006 | Pynson et al. |
| 2006/0167466 A1 | 7/2006 | Dusek |
| 2006/0173540 A1 | 8/2006 | Vincent |
| 2006/0200167 A1 | 9/2006 | Peterson et al. |
| 2006/0229633 A1 | 10/2006 | Shepherd |
| 2006/0235429 A1 | 10/2006 | Lee et al. |
| 2006/0293694 A1 | 12/2006 | Futamura |
| 2007/0000801 A1 | 1/2007 | Mauran et al. |
| 2007/0005135 A1 | 1/2007 | Makker et al. |
| 2007/0168026 A1 | 7/2007 | Nagasaka |
| 2007/0173860 A1 | 7/2007 | Iwasaki |
| 2007/0270945 A1 | 11/2007 | Kobayashi |
| 2008/0027460 A1 | 1/2008 | Kobayashi |
| 2008/0033449 A1 | 2/2008 | Cole et al. |
| 2008/0058830 A1 | 3/2008 | Cole et al. |
| 2008/0086146 A1 | 4/2008 | Ishii et al. |
| 2008/0097459 A1 | 4/2008 | Kammerlander et al. |
| 2008/0221584 A1 | 9/2008 | Downer |
| 2009/0036898 A1 | 2/2009 | Ichinohe |
| 2009/0043313 A1 | 2/2009 | Ichinohe |
| 2009/0112223 A1 | 4/2009 | Downer et al. |
| 2009/0125034 A1 | 5/2009 | Pynson |
| 2009/0138022 A1 | 5/2009 | Tu et al. |
| 2009/0204122 A1 | 8/2009 | Ichinohe et al. |
| 2009/0216244 A1 | 8/2009 | Pynson |
| 2009/0248031 A1 | 10/2009 | Ichinohe |
| 2009/0270876 A1 | 10/2009 | Hoffmann et al. |
| 2009/0292293 A1 | 11/2009 | Bogaert et al. |
| 2010/0082037 A1 | 4/2010 | Kobayashi et al. |
| 2010/0094309 A1 | 4/2010 | Boukhny et al. |

(56) References Cited

U.S. PATENT DOCUMENTS

| | | | |
|---|---|---|---|
| 2010/0106160 A1* | 4/2010 | Tsai | A61F 2/167 606/107 |
| 2010/0161049 A1 | 6/2010 | Inoue | |
| 2010/0185206 A1 | 7/2010 | Ichinohe et al. | |
| 2010/0217273 A1 | 8/2010 | Someya et al. | |
| 2010/0286704 A1 | 11/2010 | Ichinohe et al. | |
| 2010/0331808 A1 | 12/2010 | Py et al. | |
| 2011/0046633 A1 | 2/2011 | Pankin et al. | |
| 2011/0046635 A1 | 2/2011 | Pankin et al. | |
| 2011/0082463 A1 | 4/2011 | Inoue | |
| 2011/0098717 A1 | 4/2011 | Inoue | |
| 2011/0144654 A1 | 6/2011 | Isaacs et al. | |
| 2011/0172676 A1 | 7/2011 | Chen | |
| 2011/0264101 A1* | 10/2011 | Inoue | A61F 2/1672 606/107 |
| 2011/0270264 A1 | 11/2011 | Shoji et al. | |
| 2011/0288557 A1 | 11/2011 | Kudo et al. | |
| 2012/0022548 A1 | 1/2012 | Zacharias | |
| 2012/0022549 A1 | 1/2012 | Someya et al. | |
| 2012/0071887 A1 | 3/2012 | Ichinohe et al. | |
| 2012/0123438 A1 | 5/2012 | Horvath et al. | |
| 2012/0221102 A1 | 8/2012 | Tanaka et al. | |
| 2013/0006259 A1 | 1/2013 | Sanger | |
| 2013/0018460 A1 | 1/2013 | Anderson | |
| 2013/0085507 A1 | 4/2013 | Nagasaka | |
| 2013/0226193 A1 | 8/2013 | Kudo et al. | |
| 2013/0245635 A1 | 9/2013 | Inoue | |
| 2013/0345713 A1 | 12/2013 | Cole et al. | |
| 2014/0081284 A1 | 3/2014 | Ichinohe et al. | |
| 2014/0107660 A1 | 4/2014 | Ichinohe et al. | |
| 2014/0114323 A1 | 4/2014 | Kudo et al. | |
| 2014/0135784 A1 | 5/2014 | Maroscheck et al. | |
| 2014/0180299 A1 | 6/2014 | Ichinohe et al. | |
| 2014/0180300 A1 | 6/2014 | Ichinohe et al. | |
| 2014/0194890 A1 | 7/2014 | Kudo et al. | |
| 2014/0200588 A1 | 7/2014 | Anderson et al. | |
| 2014/0276901 A1 | 9/2014 | Auld | |
| 2014/0296863 A1 | 10/2014 | Anderson et al. | |
| 2015/0045805 A1 | 2/2015 | Kontur et al. | |
| 2015/0157500 A1 | 6/2015 | Midorikawa | |
| 2015/0327992 A1 | 11/2015 | Wagner et al. | |
| 2016/0000556 A1 | 1/2016 | Perera | |
| 2016/0058554 A1 | 3/2016 | Anderson et al. | |
| 2016/0113759 A1 | 4/2016 | Inoue | |
| 2016/0151150 A1 | 6/2016 | Sato | |
| 2016/0193038 A1 | 7/2016 | Kudo et al. | |
| 2016/0256316 A1 | 9/2016 | Van Noy et al. | |
| 2016/0270907 A1 | 9/2016 | Attinger | |
| 2016/0331587 A1 | 11/2016 | Yamada et al. | |
| 2016/0346077 A1 | 12/2016 | Someya et al. | |
| 2017/0079772 A1* | 3/2017 | Kudo | A61F 2/1675 |
| 2017/0119522 A1 | 5/2017 | Auld et al. | |
| 2017/0151056 A1 | 6/2017 | Inoue | |
| 2017/0202662 A1 | 7/2017 | Someya et al. | |
| 2017/0252149 A1 | 9/2017 | Kudo et al. | |
| 2017/0252150 A1 | 9/2017 | Kudo et al. | |
| 2017/0258582 A1 | 9/2017 | Kudo et al. | |
| 2017/0354493 A1 | 12/2017 | Andersen et al. | |
| 2018/0014996 A1 | 1/2018 | Asbaghi | |
| 2018/0200046 A1 | 7/2018 | Brown et al. | |
| 2018/0250125 A1 | 9/2018 | Kudo et al. | |
| 2018/0353287 A1 | 12/2018 | Kudo et al. | |
| 2019/0151078 A1 | 5/2019 | Watanabe et al. | |
| 2019/0192284 A1 | 6/2019 | Watanabe et al. | |
| 2020/0113674 A1 | 4/2020 | Someya et al. | |
| 2021/0161653 A1 | 6/2021 | Noda et al. | |
| 2022/0151767 A1 | 5/2022 | Kudo | |
| 2023/0033115 A1 | 2/2023 | Watanabe et al. | |
| 2023/0225858 A1 | 7/2023 | Someya et al. | |
| 2023/0301833 A1 | 9/2023 | Wu | |
| 2023/0372083 A1 | 11/2023 | Kudo | |
| 2024/0374376 A1 | 11/2024 | Noda et al. | |

FOREIGN PATENT DOCUMENTS

| | | |
|---|---|---|
| DE | 3610925 | 10/1987 |
| DE | 4110278 | 10/1992 |
| DE | 19544119 A1 | 5/1997 |
| DE | 20219445 U1 | 3/2003 |
| EP | 0363213 | 4/1990 |
| EP | 0727966 | 9/2003 |
| EP | 1360947 A1 | 11/2003 |
| EP | 1502559 A1 | 2/2005 |
| EP | 1790317 A2 | 5/2007 |
| EP | 1808150 A1 | 7/2007 |
| EP | 1832247 A1 | 9/2007 |
| EP | 1338254 | 12/2008 |
| EP | 2074961 A1 | 7/2009 |
| EP | 2255751 A1 | 12/2010 |
| EP | 2286763 A1 | 2/2011 |
| EP | 2286764 A1 | 2/2011 |
| EP | 2368526 A1 | 9/2011 |
| EP | 2574308 A2 | 4/2013 |
| EP | 2853236 A2 | 4/2015 |
| EP | 3391855 A1 | 10/2018 |
| FR | 2749752 A | 12/1997 |
| JP | 63-197453 A | 8/1988 |
| JP | 4-212350 A | 8/1992 |
| JP | 5-103803 A | 4/1993 |
| JP | 5-103808 | 4/1993 |
| JP | 5-103809 | 4/1993 |
| JP | 08-019558 A | 1/1996 |
| JP | 8-024282 A | 1/1996 |
| JP | 8-505540 | 6/1996 |
| JP | 9-506285 A | 6/1997 |
| JP | 11-113939 A | 4/1999 |
| JP | 11-506357 A | 6/1999 |
| JP | 2000-516487 A | 12/2000 |
| JP | 2000-516488 A | 12/2000 |
| JP | 2001-502563 | 2/2001 |
| JP | 2001-104347 A | 4/2001 |
| JP | 2001-259033 | 9/2001 |
| JP | 2002-516709 A | 6/2002 |
| JP | 2002-355268 A | 12/2002 |
| JP | 2002-541912 A | 12/2002 |
| JP | 2003-144480 A | 5/2003 |
| JP | 3412106 B2 | 6/2003 |
| JP | 2003-210498 A | 7/2003 |
| JP | 2003-527162 A | 9/2003 |
| JP | 2003-325569 A | 11/2003 |
| JP | 2003-325570 A | 11/2003 |
| JP | 2003-325572 A | 11/2003 |
| JP | 2004-024854 A | 1/2004 |
| JP | 2004-041271 A | 2/2004 |
| JP | 2004-188194 A | 7/2004 |
| JP | 2004-344213 A | 12/2004 |
| JP | 2004-351196 A | 12/2004 |
| JP | 2006-014963 A | 1/2006 |
| JP | 2006-181269 A | 7/2006 |
| JP | 2006-297146 A | 11/2006 |
| JP | 2006-333924 A | 12/2006 |
| JP | 2006-333980 A | 12/2006 |
| JP | 2006-333981 A | 12/2006 |
| JP | 2007-503872 A | 3/2007 |
| JP | 2007-152010 A | 6/2007 |
| JP | 2007-181604 A | 7/2007 |
| JP | 2007-222309 A | 9/2007 |
| JP | 2007-244570 A | 9/2007 |
| JP | 2007-526091 A | 9/2007 |
| JP | 2007-307168 A1 | 11/2007 |
| JP | 2008-012016 A | 1/2008 |
| JP | 2008-521535 A | 6/2008 |
| JP | 2008-212689 A | 9/2008 |
| JP | 2008-237274 A | 10/2008 |
| JP | 2009-008223 A | 2/2009 |
| JP | 2009-072221 A | 4/2009 |
| JP | 2011-019987 A | 2/2011 |
| JP | 2011-087976 A | 5/2011 |
| JP | 2011-160858 A | 8/2011 |
| JP | 2011-160859 A | 8/2011 |
| JP | 2013-144163 A | 7/2013 |
| JP | 2014-050484 A | 3/2014 |

(56) References Cited

FOREIGN PATENT DOCUMENTS

| | | | |
|---|---|---|---|
| JP | 2014-079630 A | 5/2014 | |
| JP | 2016-137122 A | 8/2016 | |
| WO | WO9407436 A1 | 4/1994 | |
| WO | WO9513022 A1 | 5/1995 | |
| WO | WO9628122 A1 | 9/1996 | |
| WO | WO9715253 A1 | 5/1997 | |
| WO | WO9812969 A1 | 4/1998 | |
| WO | WO9937247 A1 | 7/1999 | |
| WO | WO9958086 A1 | 11/1999 | |
| WO | WO9959668 A1 | 11/1999 | |
| WO | WO0045746 A1 | 8/2000 | |
| WO | WO0062712 A1 | 10/2000 | |
| WO | WO2002071982 A1 | 9/2002 | |
| WO | WO2002096322 A1 | 12/2002 | |
| WO | WO2004/041323 A2 | 5/2004 | |
| WO | WO2004105649 A1 | 12/2004 | |
| WO | WO2005023154 A1 | 3/2005 | |
| WO | WO2005030097 A1 | 4/2005 | |
| WO | WO2005070341 A1 | 8/2005 | |
| WO | WO2005084588 A1 | 9/2005 | |
| WO | WO2006070628 A1 | 7/2006 | |
| WO | WO2006080191 A1 | 8/2006 | |
| WO | WO2006090531 A1 | 8/2006 | |
| WO | WO2007037223 A1 | 4/2007 | |
| WO | WO2007097221 A1 | 4/2007 | |
| WO | WO2007080869 A1 | 7/2007 | |
| WO | WO2008149794 A1 | 12/2008 | |
| WO | WO2008149795 A1 | 12/2008 | |
| WO | WO2009058929 A1 | 7/2009 | |
| WO | WO2009148091 A1 | 12/2009 | |
| WO | WO2010028873 A1 | 3/2010 | |
| WO | WO2010064970 A1 | 6/2010 | |
| WO | WO2011126144 A1 | 10/2011 | |
| WO | WO2011155636 A1 | 12/2011 | |
| WO | WO2012086797 A1 | 6/2012 | |
| WO | WO2012155887 A1 | 11/2012 | |
| WO | WO2015012312 A1 | 1/2015 | |
| WO | WO2016191764 A1 | 12/2016 | |
| WO | WO2019130028 A1 | 7/2019 | |

OTHER PUBLICATIONS

EPO Extended European Search Report dated May 6, 2022 for EPO App. Ser. No. 19803973.7.
English Translation of PCT International Preliminary Examination Report dated Nov. 26, 2020 for PCT App. Ser. No. PCT/JP2019/017744.
U.S. Appl. No. 18/186,167, filed Mar. 18, 2023, US 20230225858A1.
U.S. Appl. No. 13/059,401, filed Feb. 16, 2011, U.S. Pat. No. 9,980,811.
U.S. Appl. No. 14/065,365, filed Oct. 28, 2013, U.S. Pat. No. 8,460,311.
U.S. Appl. No. 16/313,184, filed Dec. 26, 2018, US 20190151078A1.
U.S. Appl. No. 17/055,253, filed Nov. 13, 2020.
U.S. Appl. No. 17/055,186, filed Nov. 13, 2020.
U.S. Appl. No. 17/801,364 filed Aug. 22, 2022.
U.S. Appl. No. 18/186,167, filed Mar. 18, 2023.
U.S. Appl. No. 18/044,235, filed Mar. 7, 2023.
U.S. Appl. No. 17/005,186, filed Nov. 13, 2020, US 20210145570A1.
U.S. Appl. No. 17/435,762, filed Sep. 2, 2021.
U.S. Appl. No. 16/550,144, filed Aug. 23, 2019, US 20200113674A1.
PCT International Search Report dated Jun. 18, 2019 for PCT App. Ser. No. PCT/JP2019/017744.
U.S. Appl. No. 13/966,209, filed Aug. 13, 2013, U.S. Pat. No. 9,364,320.
U.S. Appl. No. 17/055,253, filed Nov. 13, 2020, US 20210161653A1.
U.S. Appl. No. 12/602,442, filed Dec. 15, 2009, U.S. Pat. No. 8,747,465.
U.S. Appl. No. 13/244,449, filed Sep. 24, 2011, U.S. Pat. No. 9,289,288.
U.S. Appl. No. 15/063,395, filed Mar. 7, 2016, U.S. Pat. No. 10,390,940.
U.S. Appl. No. 15/476,717, filed Mar. 31, 2017, U.S. Pat. No. 10,405,971.
U.S. Appl. No. 16/550,144, filed Aug. 23, 2019, U.S. Pat. No. 11,617,643.
U.S. Appl. No. 18/186,167, filed Mar. 18, 2023, U.S. Pat. No. 11,938,019.
U.S. Appl. No. 12/602,454, filed Dec. 15, 2009, U.S. Pat. No. 8,475,528.
U.S. Appl. No. 13/244,452, filed Sep. 24, 2011, U.S. Pat. No. 8,535,375.
U.S. Appl. No. 12/667,510, filed Dec. 31, 2009, U.S. Pat. No. 9,114,006.
U.S. Appl. No. 14/812,104, filed Jul. 29, 2015, U.S. Pat. No. 9,907,647.
U.S. Appl. No. 12/995,263, filed Dec. 15, 2010, U.S. Pat. No. 9,554,894.
U.S. Appl. No. 15/382,377, filed Dec. 16, 2016, U.S. Pat. No. 10,517,717.
U.S. Appl. No. 12/997,651, filed Dec. 13, 2010, U.S. Pat. No. 8,382,769.
U.S. Appl. No. 13/757,790, filed Feb. 2, 2012, U.S. Pat. No. 9,186,246.
U.S. Appl. No. 13/583,216, filed Apr. 6, 2011, U.S. Pat. No. 9,326,847.
U.S. Appl. No. 13/699,708, filed Jun. 8, 2011, U.S. Pat. No. 8,647,382.
U.S. Appl. No. 14/145,846, filed Dec. 31, 2013, U.S. Pat. No. 9,314,373.
U.S. Appl. No. 15/071,880, filed Mar. 16, 2016, U.S. Pat. No. 10,039,668.
U.S. Appl. No. 15/336,678, filed Oct. 27, 2016, U.S. Pat. No. 9,572,710.
U.S. Appl. No. 15/608,895, filed May 30, 2017, U.S. Pat. No. 9,980,811.
U.S. Appl. No. 13/059,401, filed Feb. 16, 2011, U.S. Pat. No. 8,702,795.
U.S. Appl. No. 13/061,143, filed Feb. 26, 2011, U.S. Pat. No. 8,470,032.
U.S. Appl. No. 13/143,322, filed Jul. 5, 2011, U.S. Pat. No. 8,603,103.
U.S. Appl. No. 14/099,989, filed Dec. 8, 2013, U.S. Pat. No. 9,655,718.
U.S. Appl. No. 15/600,679, filed May 19, 2017, U.S. Pat. No. 9,877,826.
U.S. Appl. No. 15/600,684, filed May 19, 2017, U.S. Pat. No. 9,901,442.
U.S. Appl. No. 11/814,508, filed Jul. 23, 2007, U.S. Pat. No. 8,545,512.
U.S. Appl. No. 14/033,888, filed Sep. 23, 2013, U.S. Pat. No. 9,220,593.
U.S. Appl. No. 11/816,676, filed Aug. 20, 2007, U.S. Pat. No. 8,523,877.
U.S. Appl. No. 13/966,209, filed Aug. 13, 2013, U.S. Pat. No. 9,634,320.
U.S. Appl. No. 12/095,172, filed May 28, 2008, U.S. Pat. No. 8,523,941.
U.S. Appl. No. 14/011,018, filed Aug. 27, 2013, U.S. Pat. No. 8,968,328.
U.S. Appl. No. 12/088,328, filed Mar. 27, 2008, U.S. Pat. No. 8,574,239.
U.S. Appl. No. 14/065,365, filed Oct. 28, 2013, U.S. Pat. No. 9,114,007.
U.S. Appl. No. 11/722,601, filed Apr. 10, 2008, U.S. Pat. No. 8,460,311.
U.S. Appl. No. 15/126,277, filed Sep. 14, 2016, U.S. Pat. No. 10,383,723.
U.S. Appl. No. 15/756,565, filed Feb. 28, 2018, U.S. Pat. No. 10,849,738.
U.S. Appl. No. 15/756,569, filed Feb. 28, 2018, U.S. Pat. No. 10,799,339.
U.S. Appl. No. 16/313,180, filed Dec. 26, 2018, US 20190192284A1.
U.S. Appl. No. 16/313,184, filed Dec. 26, 2018, U.S. Pat. No. 11,033,382.

(56) References Cited

OTHER PUBLICATIONS

U.S. Appl. No. 17/055,253, filed Nov. 13, 2020, U.S. Pat. No. 12,076,231.
U.S. Appl. No. 18/778,973, filed Jul. 20, 2024, US 20240374376A1.
U.S. Appl. No. 17/055,186, filed Nov. 13, 2020, US 20210145570A1.
U.S. Appl. No. 17/435,762, filed Sep. 2, 2021, US 20220151767A1.
U.S. Appl. No. 17/801,364, filed Aug. 22, 2022, US 20230033115A1.
U.S. Appl. No. 18/044,235, filed Mar. 7, 2023, US 20230372083A1.
U.S. Appl. No. 18/694,985, filed Mar. 24, 2023.

* cited by examiner

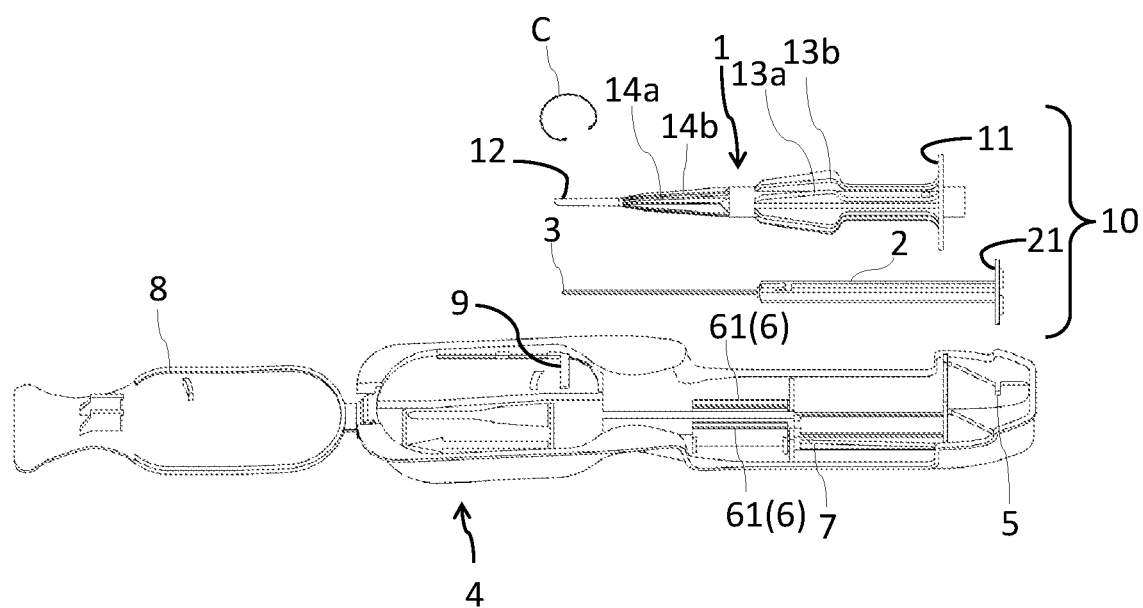
FIG. 1
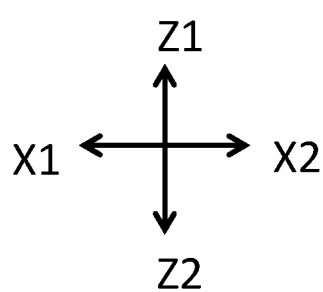

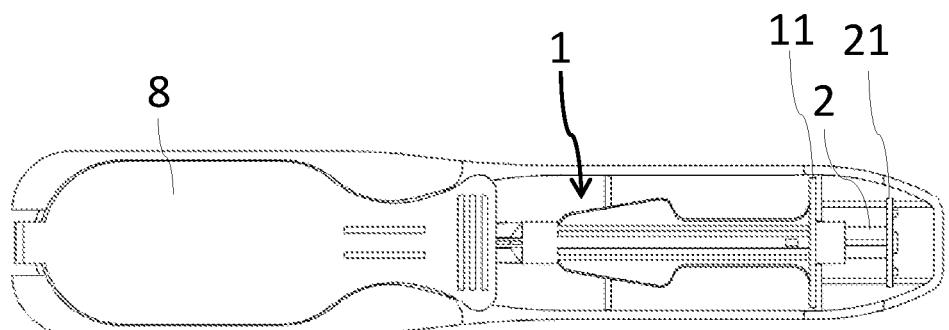
FIG. 5A
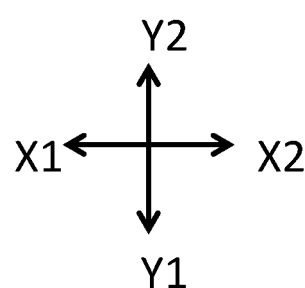
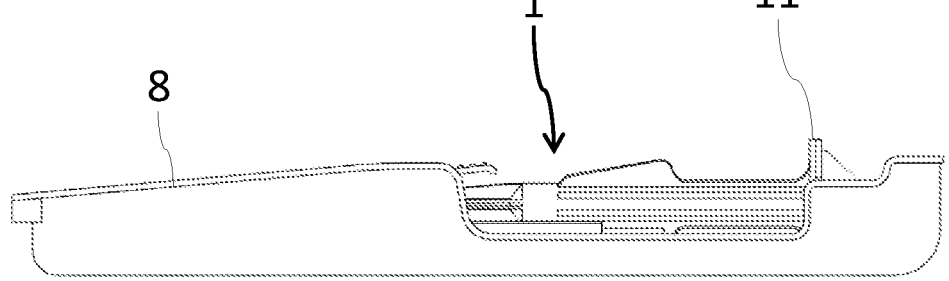
FIG. 5B
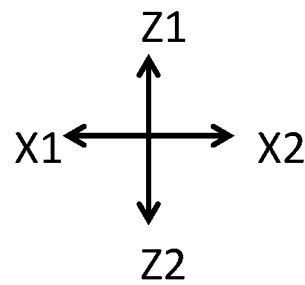

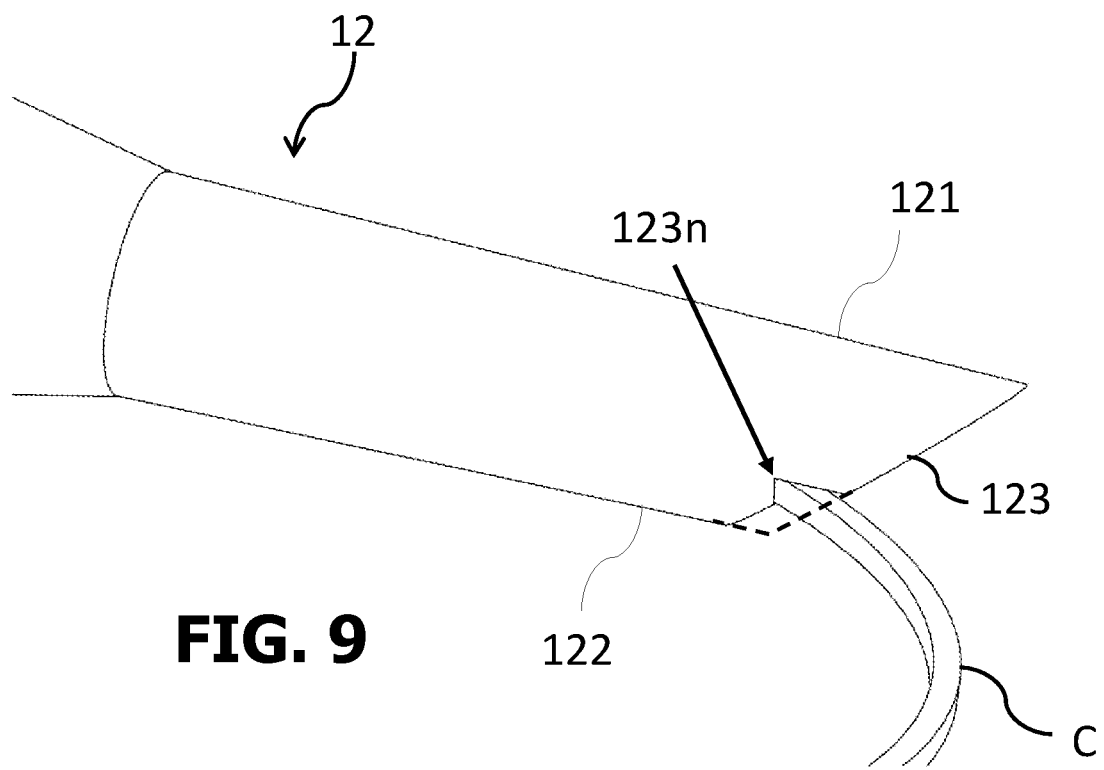
FIG. 9
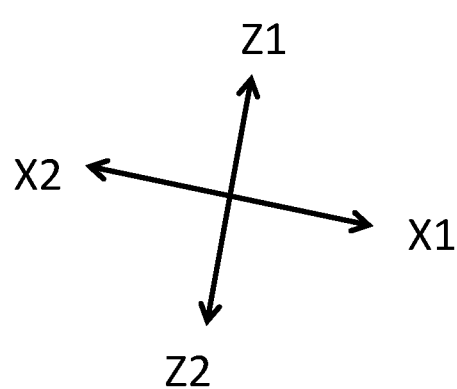

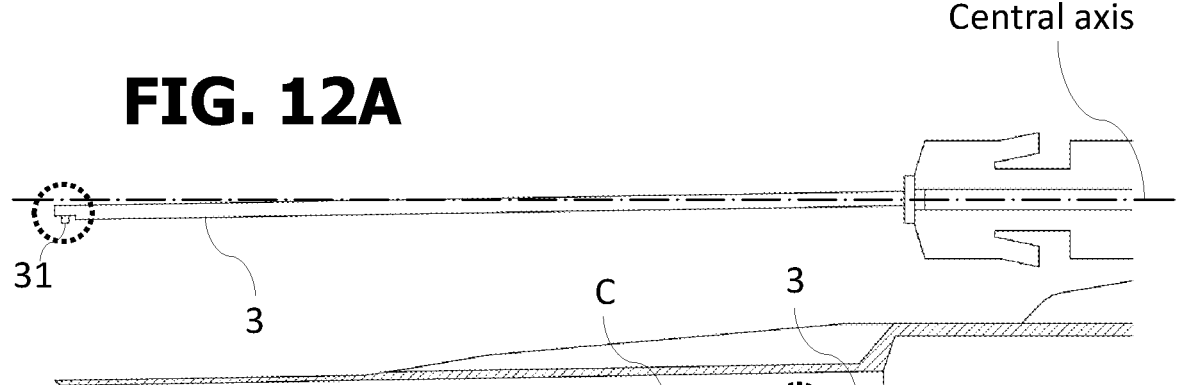

INTRAOCULAR LENS INJECTOR WITH CONTAINER

TECHNICAL FIELD

The present invention relates to an intraocular ring injector with a container.

DESCRIPTION OF RELATED ART

One of the treatment methods for cataract is a method using an intraocular lens. In this treatment method, lens fibers (nucleus, cortex) are removed from a lens capsule by extracapsular cataract extraction, and then an intraocular lens is injected into the lens capsule. In that case, prior to the injection of the intraocular lens, a capsular tension ring (CTR) may be sometimes placed as an intraocular ring into the lens capsule after the extracapsular cataract extraction, in order to retain the shape of the lens capsule. This intraocular ring is placed so as to be inscribed in the equatorial segment of the lens capsule, and retains the shape of the lens capsule by exerting an appropriate tension in this placement state (for example, FIG. 1 of Patent Document 1).

Various intraocular ring injectors have been developed for injecting such an intraocular ring into a lens capsule (for example, "ring introducer" in Patent Document 1). FIG. 6 of Patent Document 1 shows hook 56 connected to piston 48 being hooked on opening 26 of the intraocular ring. A surgeon as an operator needs only to manipulate a ring injector, which enables removal of an end part of the lens capsule ring which is an intraocular ring out of the cannula and expulsion of the lens capsule ring through the ring injector ([0028] of Patent Document 1).

PRIOR ART DOCUMENT

Patent Document

[Patent Document 1] Japanese Unexamined Patent Publication (Translation of PCT Application) No. 2003-527162

SUMMARY OF THE INVENTION

Problem to be Solved by the Invention

In a conventional intraocular ring injector, a member that pushes out an intraocular ring (in Patent Document 1, wire 54 having hook 56) is fitted into a hole (hereinafter referred to as an eyelet) of the intraocular ring. After that, the plunger (piston 72 in Patent Document 1) is moved rearward. As a result, the intraocular ring is housed in the intraocular ring injector. A nozzle, which is a tip end of the intraocular ring injector, is then injected into a lens capsule through an incision in the patient's cornea. Subsequently, the intraocular ring is injected into the lens capsule through the nozzle.

Among the above operations, an operation of moving the plunger rearward must be performed while maintaining the engagement between the pushing member of the intraocular ring injector and the eyelet of the intraocular ring. The engagement may be released upon such an operation by the operator. Besides, a problem occurring in the intraocular ring while the operator is distracted by the movement of the plunger may be less likely to noticed by the operator.

An object of the present invention is to provide an intraocular ring injector that allows an operator to stably and normally make an intraocular ring be housed into the intraocular ring injector.

Means for Solving the Problem

With the conventional intraocular ring injector, an operation to make the intraocular ring be housed in the intraocular ring injector is performed outside the container for housing the intraocular ring injector. The present inventor paid attention to this point and found that the above-mentioned housing operation is to be completed in the container.

The configurations obtained based on the above findings are as follows.

A first aspect of the present invention is an intraocular ring injector with a container configured so that the intraocular ring injector is housed in the container, for injecting an intraocular ring into an eye for retaining a shape of a lens capsule, the intraocular ring injector including:
a hollow body having a hollow part in which the intraocular ring is housed;
a plunger that moves through an inside of the hollow body in an axial direction of the hollow body; and
a pushing member that pushes out the intraocular ring by moving together with the plunger through the inside of the hollow body and toward front part of the hollow body in the axial direction,
wherein the container has a moving mechanism of moving the hollow body and the plunger relatively in the axial direction, while housing the intraocular ring injector in the container.

A second aspect of the present invention is the invention according to the first aspect, including a movement restricting portion that restricts a movement of the intraocular ring injector while being housed in the container, in a direction other than the axial direction.

A third aspect of the present invention is the invention according to the second aspect, wherein the movement restricting portion cancels restriction of the movement of the intraocular ring injector, when the hollow body and the plunger are relatively moved by a distance for housing the intraocular ring in the hollow body, the intraocular ring being engaged with an axial end of the pushing member.

A fourth aspect of the present invention is the invention according to the third aspect, wherein the distance is 20 to 50 mm.

A fifth aspect of the present invention is the invention according to any one of the first to fourth aspects, wherein the container includes:
a plunger movement restricting portion that restricts a movement of the plunger in the axial direction, while housing the intraocular ring injector in the container; and
a hollow body movement restricting portion that restricts the movement of the hollow body in a direction other than the axial direction, while permitting the movement of the hollow body in the axial direction, while housing the intraocular ring injector in the container.

A sixth aspect of the present invention is the invention according to the fifth aspect, wherein the hollow body movement restricting portion cancels the restriction of the movement of the hollow body, when the hollow body moves forward by the distance for housing the intraocular ring in the hollow body, the intraocular ring being engaged with an axial end of the pushing member.

A seventh aspect of the present invention is the invention according to the fifth or sixth aspect, wherein a plurality of hollow body movement restricting portions are provided.

An eighth aspect of the present invention is the invention according to any one of the fifth to seventh aspects, wherein the hollow body movement restricting portion is engaged with an outer circumference of the hollow body in the axial direction.

A ninth aspect of the present invention is the invention according to any one of the fifth to eighth aspects, wherein the hollow body movement restricting portion further has a return restricting portion that restricts the hollow body from moving rearward in the axial direction.

A tenth aspect of the present invention is the invention according to any one of the fifth to ninth aspects, wherein the plunger movement restricting portion is a groove that engages with a rear end of the plunger in the axial direction.

An eleventh aspect of the present invention is the invention according to any one of the first to tenth aspects, wherein the hollow body has a nozzle for releasing the intraocular ring from an opening, and the nozzle has a shape in which one end is long and the other end is the same or short, and a short one end side of the opening of the nozzle is cut out, in a side view which is a direction perpendicular to the axial direction of the hollow body.

A twelfth aspect of the present invention is the invention according to any one of the first to eleventh aspects, wherein the hollow body has the nozzle for releasing the intraocular ring from the opening, and an overhanging portion is provided to at least a part of the pushing member in the axial direction, for preventing backflow of an aqueous humor from the opening of the nozzle.

A thirteenth aspect of the present invention is the invention according to any one of the first to twelfth aspects, wherein at least a front portion of the pushing member on which a protrusion is provided, is displaced from the axial direction of the plunger to a direction in which the protrusion is protruded.

A fourteenth aspect of the present invention is the invention according to any one of the first to thirteenth aspects, further including an intraocular ring.

Another aspect of the present invention is as follows.

An injector for injecting an intraocular ring for retaining a shape of a lens capsule or an intraocular lens into an eye, including a nozzle for releasing the intraocular ring or the intraocular lens, wherein the nozzle has a shape in which one end is long and the other end is the same or short, and the same or short end side of the opening of the nozzle is cut out, in a side view which is a direction perpendicular to the releasing direction.

Preferably, with respect to a cutout on the same or short end side, an additional cutout is provided rearward at the position closer to the short end relative to a midpoint between an upper long end and a lower short end of the nozzle.

Still another aspect of the present invention is as follows.

An intraocular ring injector for injecting an intraocular ring into an eye for retaining a shape of a lens capsule, the intraocular ring injector including:
a hollow body having a hollow part in which the intraocular ring is housed;
a plunger that moves through an inside of the hollow body in an axial direction of the hollow body; and
a pushing member that pushes out the intraocular ring by moving together with the plunger through the inside of the hollow body and toward front part of the hollow body in the axial direction,
wherein the hollow body has the nozzle for releasing the intraocular ring from the opening, and an overhanging portion is provided to at least a part of the pushing member in the axial direction, for preventing backflow of an aqueous humor from the opening of the nozzle.

Still another aspect of the present invention is as follows.

An intraocular ring injector for injecting an intraocular ring into an eye for retaining a shape of a lens capsule, the intraocular ring injector including:
a hollow body having a hollow part in which the intraocular ring is housed;
a plunger that moves through an inside of the hollow body in an axial direction of the hollow body; and
a pushing member that pushes out the intraocular ring by moving together with the plunger through the inside of the hollow body and toward front part of the hollow body in the axial direction,
wherein at least a front portion of the pushing member on which a protrusion for engagement with the intraocular ring is provided, is displaced from the axial direction of the plunger to a direction in which the protrusion is protruded.

SUMMARY OF THE INVENTION

According to the present invention, the intraocular ring can be stably and normally housed in the intraocular ring injector.

BRIEF DESCRIPTION OF THE DRAWINGS

FIG. 1 is an exploded schematic perspective view of an intraocular ring injector with a container of this embodiment.

FIG. 5(*a*) is a schematic plan view of the intraocular ring injector with a container of this embodiment, with a lid of the container closed, and FIG. 5(*b*) is a side view thereof.

FIG. 9 is a schematic side view of the nozzle of the intraocular ring injector of this embodiment.

FIG. 12(*a*) is a schematic side view illustrating a pushing member of the intraocular ring injector of this embodiment, and FIG. 12(*b*) is a schematic side view illustrating the vicinity of a nozzle of the intraocular ring injector of this embodiment.

DETAILED DESCRIPTION OF THE INVENTION

Embodiments of the present invention will be described hereafter, with reference to the drawings. In the present specification, "to" refers to a predetermined value or more and a predetermined value or less.

FIG. 1 is an exploded schematic perspective view of intraocular ring injector with a container 20 of this embodiment.

Figure 2:
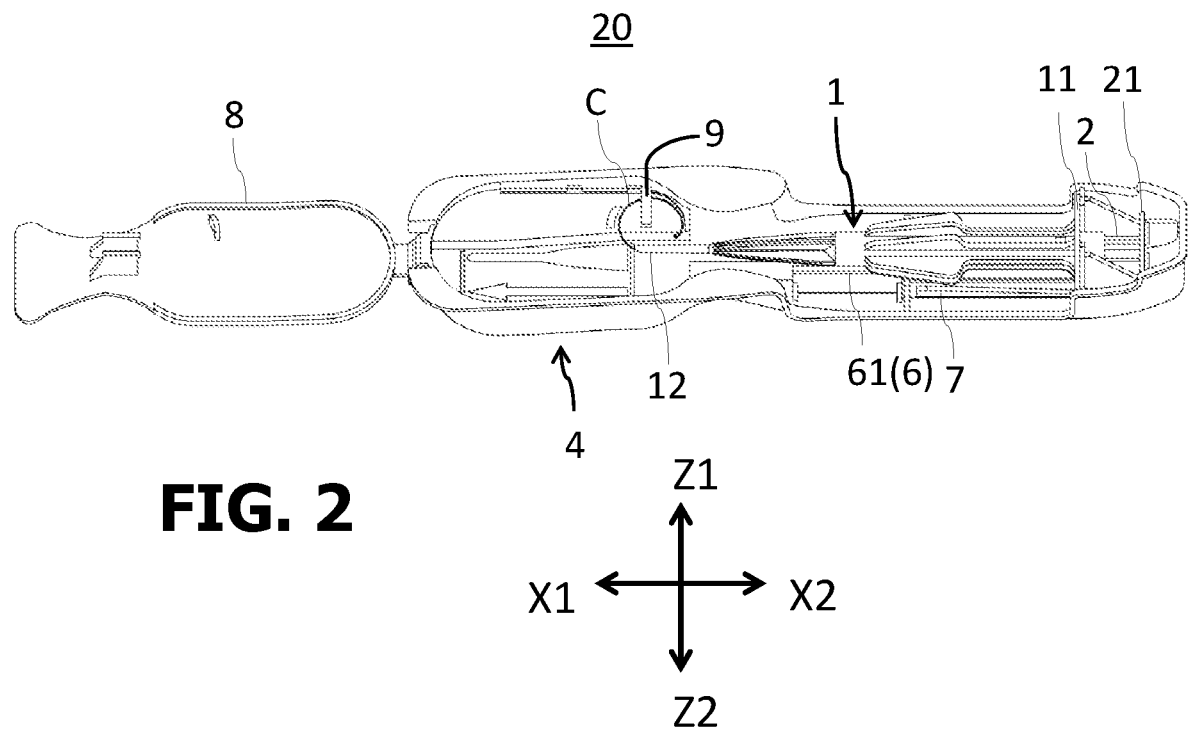
FIG. 2 is a schematic perspective view of the intraocular ring injector with a container of this embodiment.

FIG. 2 is a schematic perspective view of the intraocular ring injector with a container 20 of this embodiment.

Figure 3:
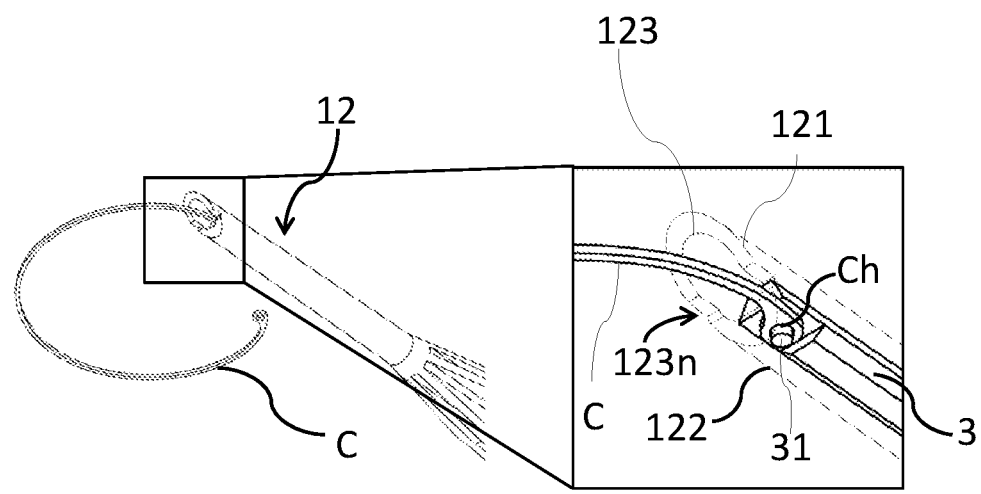
FIG. 3 is a schematic perspective view illustrating an intraocular ring placed in the intraocular ring injector of this embodiment.

FIG. 3 is a schematic perspective view illustrating an intraocular ring C placed in the intraocular ring injector 10 of this embodiment.

Figure 4:
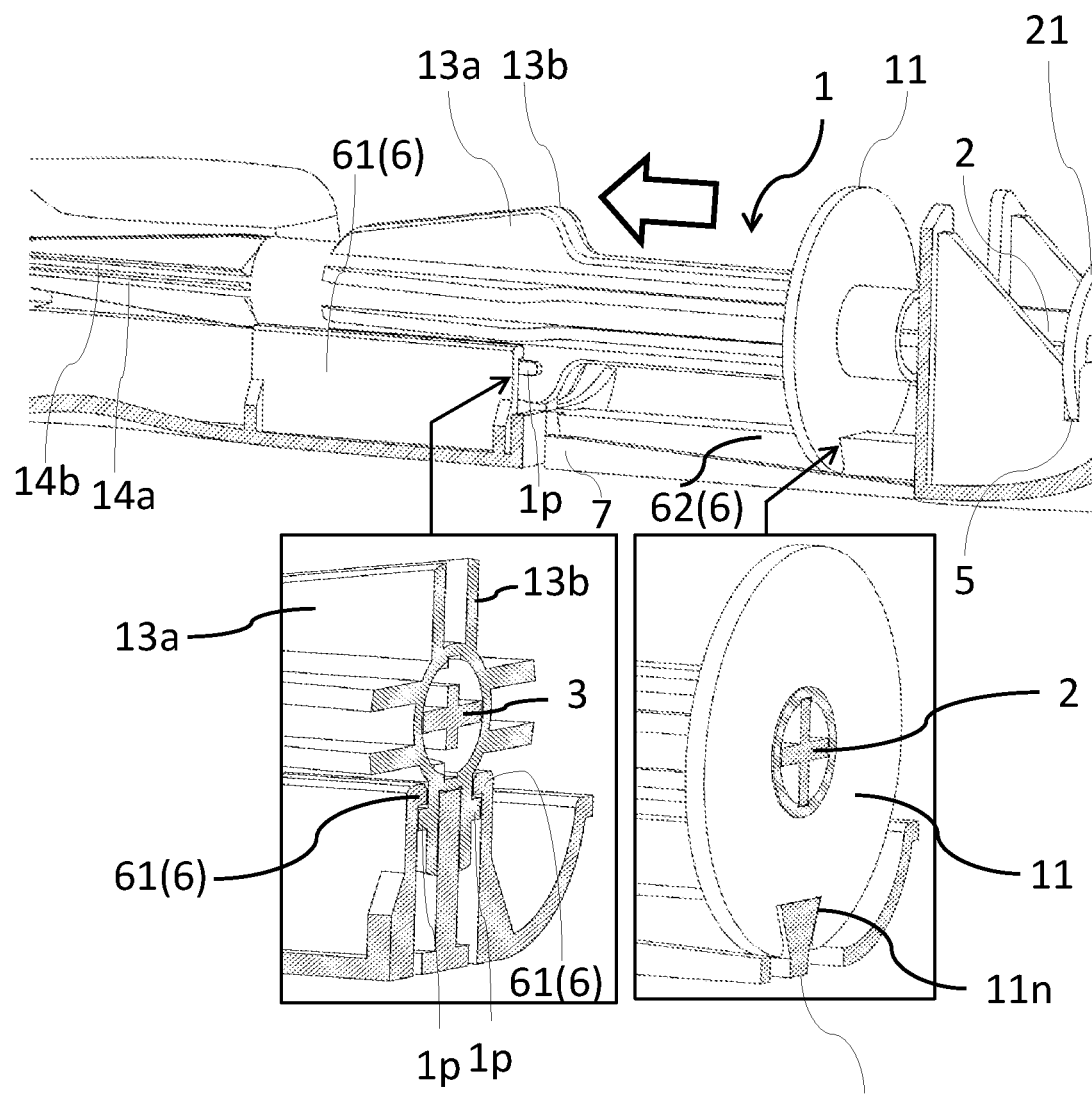
FIG. 4 is a schematic perspective view of a part of the intraocular ring injector with a container of this embodiment, before moving the hollow body.

FIG. 4 is a schematic perspective view of a part of the intraocular ring injector with a container 20 of this embodiment.

Further, in this embodiment, in describing a relative positional relationship and a direction of movement and the like of each part of the intraocular ring injector 10, one of the X axis directions is defined as X1 direction, the other direction is defined as X2 direction, and one of the Y axis directions is defined as Y1 direction, the other direction is defined as Y2 direction, and one of the Z axis directions is defined as 21 direction and the other direction is defined as Z2 direction, and X1 direction is defined as a tip end side (forward), X2 direction is defined as a rear end side (rearward), Y1 direction is defined as a left side (leftward), and Y2 direction is defined as a right side (rightward), Z1 direction is defined as an upper side (upward), and Z2 direction is defined as a downside (downward). Among them, the X1 direction and X2 direction correspond to length directions of the intraocular ring injector 10, and the Y1 direction and Y2 direction correspond to width directions of the intraocular ring injector 10, and the Z1 direction and Z2 direction correspond to height directions of the intraocular ring injector 10.

The main feature portion in this embodiment is the part involved in the engagement between the intraocular ring injector 10 and the container 4. A known configuration may be used except for the portion involved in the engagement. Therefore, the intraocular ring injector 10 itself and the container 4 itself will be hereinafter illustrated in a simplified manner.

An intraocular ring C addressed in this embodiment includes a lens capsule tension ring (CTR) placed in an eye to retain the shape of a lens capsule. The CTR is formed in an open ring shape that is curved in an arc shape as a whole. An open ring shape means that a partially open ring. However, a known CTR can be used. For this reason, the description in its entirety relating to the CTR in Japanese Patent Laid-Open Publication No. 2016-214494 of the present applicant is considered to be indicated in this specification.

As illustrated in FIG. 1 and FIG. 2, this embodiment relates to intraocular ring injector with a container 20 configured so that intraocular ring injector 10 is housed in container 4, for injecting intraocular ring C into an eye for retaining a shape of a lens capsule.

Intraocular ring injector 10 includes:

hollow body 1 having a hollow part in which intraocular ring C is housed;

plunger 2 that moves through an inside of the hollow body 1 in an axial direction of the hollow body 1; and pushing member 3 that pushes out the intraocular ring C by moving together with the plunger 2 through the inside of the hollow body 1 in the axial direction of the hollow body 1.

The hollow body 1 is a main body of the intraocular ring injector 10. Nozzle 12 having opening 123 is disposed at a tip end of the hollow body 1. Flange 11 is provided at a rear end of the axial direction of the hollow body 1.

As the flange 21 of the plunger 2 is pushed, the plunger 2 moves inside the hollow body 1 in the axial direction to push the intraocular ring C out of the nozzle 12 of the hollow body 1. The plunger 2 is disposed coaxially with the hollow body 1. The plunger 2 is provided movably in the axial direction of the hollow body 1.

Pushing member 3 is formed in an elongated rod shape. The pushing member 3 is connected to the tip end part of the plunger 2 and moves integrally with the plunger 2 in the axial direction of the hollow body 1. The pushing member 3 may be integrally molded with the plunger 2.

As illustrated in FIG. 3, protrusion 31 for eyelet Ch is provided at the tip end part of pushing member 3 to face downward. When the intraocular ring C is placed on the intraocular ring injector 10, the protrusion 31 is fitted into a hole (eyelet Ch) provided in the intraocular ring C. Since the eyelet Ch is fitted into the downward protrusion 31, when the protrusion 31 of the pushing member 3 goes out from the opening 123 of the nozzle 12, the protrusion 31 is quickly released from the engagement with the eyelet Ch so that the intraocular ring C is released into the lens capsule.

The intraocular ring injector 10 of this embodiment may be a so-called preload type intraocular ring injector 10 in which the eyelet Ch of the intraocular ring C and the protrusion 31 of the pushing member 3 are engaged in advance. Of course, the eyelet Ch of the intraocular ring C and the protrusion 31 of the pushing member 3 may be engaged afterwards. However, the preload type does not require an engagement process by an operator, and therefore the intraocular ring C can be stably housed in the intraocular ring injector 10.

The container 4 housing the intraocular ring injector 10 includes a moving mechanism (or "movement control mechanism") that allows the hollow body 1 and the plunger 2 to move relatively in the axial direction, while housing the intraocular ring injector 10 in the container 4.

This moving mechanism (or "movement control mechanism") is not particularly limited so long as it can allow the hollow body 1 and the plunger 2 to move relatively in the axial direction, while housing the intraocular ring injector 10 in the container 4. For example, a sliding mechanism capable of sliding allowing at least one of the hollow body 1 and the plunger 2 to slide in the axial direction while housing the intraocular ring injector 10 in the container 4 may be used in at least one of the intraocular ring injector 10 and the container 4.

The expression "move the hollow body 1 and the plunger 2 relatively in the axial direction" means that at least one of the hollow body 1 and the plunger 2 are moved in the axial direction so that the rear end of the hollow body 1 is distanced from the rear end of the plunger 2 (for example, the flange 11 of the hollow body 1 is distanced from the flange 21 of the plunger 2). Of the hollow body 1 and the plunger 2, it may be the hollow body 1, as mainly described in this embodiment, or the plunger 2, as described in the modified example, that is to be moved. Alternatively, the hollow body 1 and the plunger 2 may be moved together.

Examples of the moving mechanism other than the above-described sliding mechanism include a movement restricting portion that restricts a movement of the intraocular ring injector 10 while being housed in the container 4, in a direction other than the axial direction. The phrase "restricts a movement of the intraocular ring injector 10 in a direction other than the axial direction" means that the intraocular ring injector 10 itself does not come out of the container 4. This state will be described.

In this embodiment, the following examples are mainly described.

The movement restricting portion includes the plunger movement restricting portion 5 and the hollow body movement restricting portion 6. In the container 4, the plunger 2 is fit in a vertical groove, which is the plunger movement restricting portion 5, downward from above and fixed, as illustrated in FIG. 4. On the other hand, the hollow body movement restricting portion 6 (protrusion 1p of the hollow body 1 and first protrusion 61 of the container, and cutout 11n of the flange of the hollow body and second protrusion 62 of the container) makes the hollow body 1 slide only in the axial direction.

In this embodiment, the plunger 2 may be movable upward when the flange 21 at the rear end of the plunger 2 is simply fit into the groove. On the other hand, the presence of the hollow body movement restricting portion 6 restricts the movement of the hollow body 1, and thus the intraocular ring injector 10 as a whole, in the direction other than the axial direction unless the hollow body 1 is moved forward by a predetermined distance.

As described above, a state where at least one of the members forming the intraocular ring injector 10 engages with the container 4 so that the intraocular ring injector 10 is prevented from moving in a direction other than the axial direction is referred to as "the movement of the intraocular ring injector in a direction other than the axial direction is restricted".

The main examples of the container 4 of this embodiment are as follows.

The container 4 housing the intraocular lens injector 10 includes:

plunger movement restricting portion 5 that restricts a movement of the plunger 2 in the axial direction (forward and backward), while housing the intraocular ring injector 10 in the container 4; and hollow body movement restricting portion 6 that restricts the movement of the hollow body 1 in a direction other than the axial direction, while permitting the movement of the hollow body 1 in the axial direction (forward and backward), while housing the intraocular ring injector 10 in the container 4.

An aspect of the plunger movement restricting portion 5 is not particularly limited so long as it can restrict a movement of the plunger 2 in the axial direction (forward and backward). For example, the plunger movement restricting portion may be a groove that engages with the flange 21 at the rear end of the plunger 2. Such a groove may be provided at one position, or two positions of right and left sides. A groove that engages with the tip end part (rod-like portion), rather than the flange 21 at the rear end of the plunger 2 may be further provided. Moreover, a ring-shaped member capable of completely fixing the plunger 2 may be used.

There is no particular limitation on an aspect of the hollow body movement restricting portion 6. For example, it may be a member having a substantially C shape which can be held by fitting the hollow body 1 through the substantially C-shaped opening portion. It is preferably configured to be able to engage with the outer circumference of the hollow body 1 in the axial direction.

In this configuration, as illustrated in FIG. 4, a protrusion 1p extending in the axial direction, that is, in the forward and backward direction, of the hollow body 1 is provided on the outer circumference of the hollow body 1, and first protrusion 61 that engages with this protrusion 1p in the axial direction may be provided on the container 4. This configuration can restrict the hollow body 1 from moving in a direction other than the axial direction.

The position where the hollow body movement restricting portion 6 is provided is not particularly limited as long as it is on the outer circumference of the hollow body 1. For example, the protrusion 1p and the first protrusion 61 may be provided at positions corresponding to the outer circumference of the main body portion before the flange 11 of the hollow body 1.

Further, the hollow body movement restricting portion 6 may be provided with respect to the flange 11 of the hollow body 1. For example, as illustrated in FIG. 4, a cutout 11n may be provided on the lower portion of the flange 11 of the hollow body 1, the cutout being tapered (wider toward the center of the hollow body 1, and narrower toward the lower edge of the flange 11 of the hollow body 1) as viewed in the forward and backward direction. In addition, a second protrusion 62 having a shape corresponding to the tapered cutout 11n, that is, a shape having a wider upper portion and a narrower lower portion, and extending in the forward and backward direction, may be provided on the container 4.

Further, a plurality of hollow body movement restricting portions 6 may be provided. For example, both of the protrusions 61 and 62 of the above two examples may be provided.

This embodiment will be hereinafter described based on specific usage aspects.

FIG. 5(a) is a schematic plan view of the intraocular ring injector with a container 20 of this embodiment, with lid 8 of the container 4 closed, and FIG. 5(b) is a side view thereof.

Figure 6A:
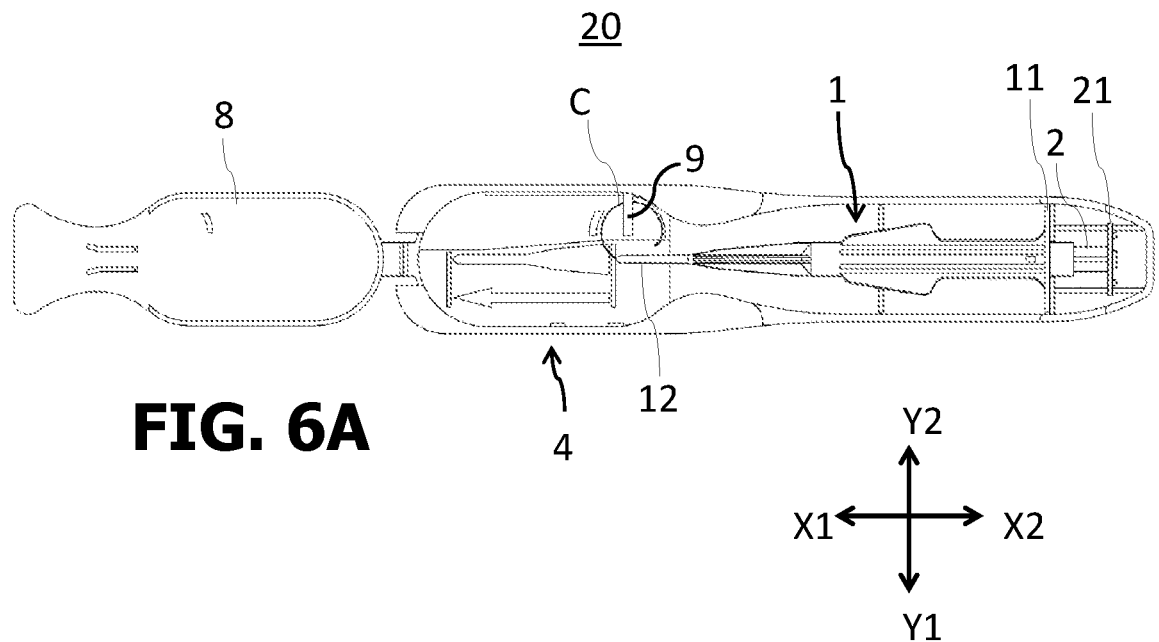
FIG. 6(*a*) is a schematic plan view of the intraocular ring injector with a container of this embodiment, with a lid of the container opened, and FIG. 6(*b*) is a side view thereof.
Figure 6B:
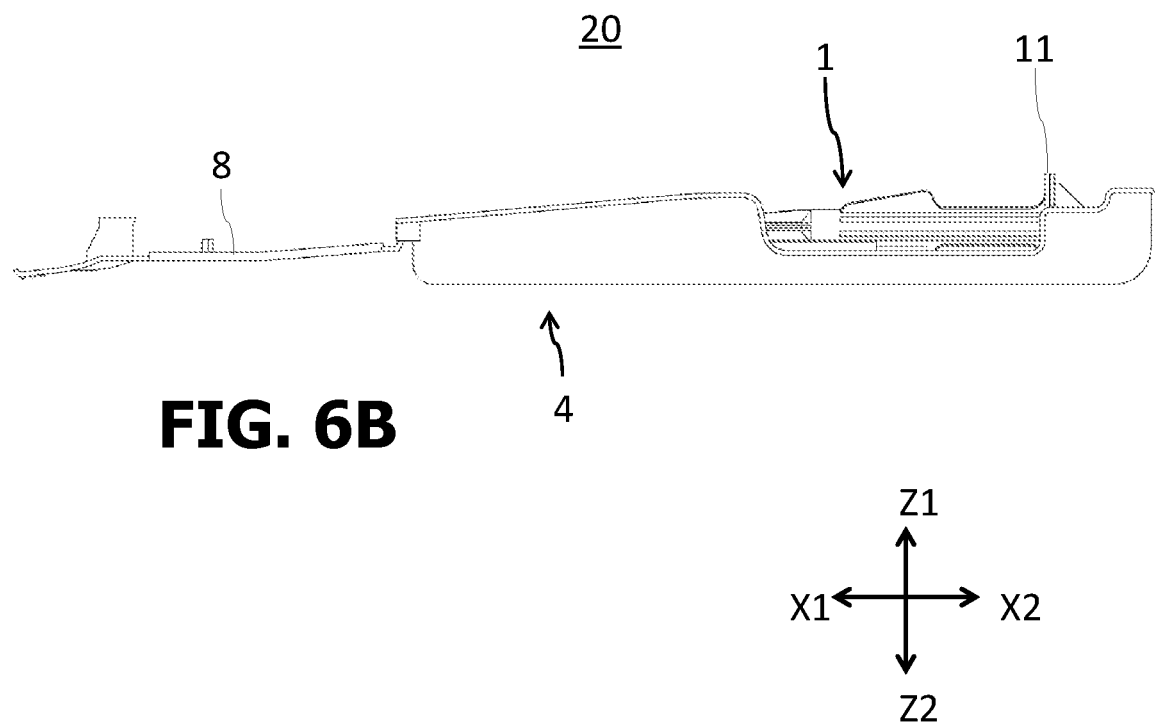

FIG. 6(a) is a schematic plan view of the intraocular ring injector with a container 20 of this embodiment, with lid 8 of the container 4 opened, and FIG. 6(b) is a side view thereof.

First, the lid 8 of the container 4 of the intraocular ring injector 10 of this embodiment is opened. That is, a state as illustrated in FIG. 5 is changed to a state as illustrated in FIG. 6. The lid 8 is provided so as to cover the tip end side of the hollow body 1, and a hinge is provided at the tip end of the container 4. When this lid 8 is opened, an operator can notice an arrow provided on the bottom of the container 4. This arrow indicates the direction in which the hollow body 1 is to be moved.

As illustrated in FIG. 2, this embodiment is of a preload type, which does not require an operation to engage the protrusion 31 of the pushing member 3 with the eyelet Ch (opening) of the intraocular ring C. Even when it is not a preload type, such engagement can be made stably while the intraocular ring injector 10 is housed in the container 4. Moreover, since the hook 9 is provided for hooking the intraocular ring C, such engagement can be made more stably. The rest of the intraocular ring C, excluding the vicinity of the eyelet Ch, is then disposed outside of the nozzle 12.

Figure 7:
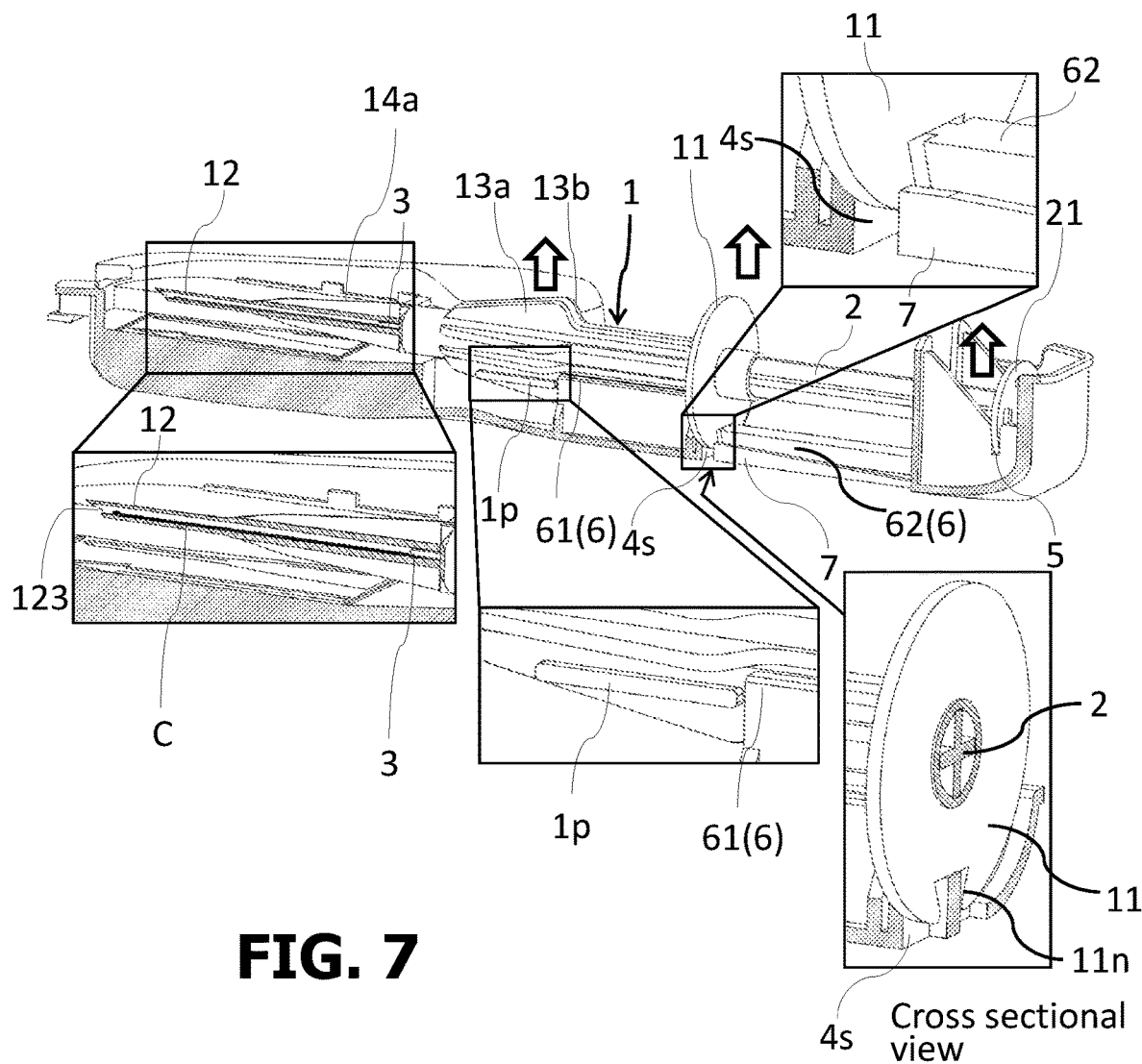
FIG. 7 is a schematic perspective view of the intraocular ring injector with a container of this embodiment (a part of the hollow body where the intraocular ring and the pushing member are present is illustrated as a transparent view), after moving the hollow body.
Figure 7:
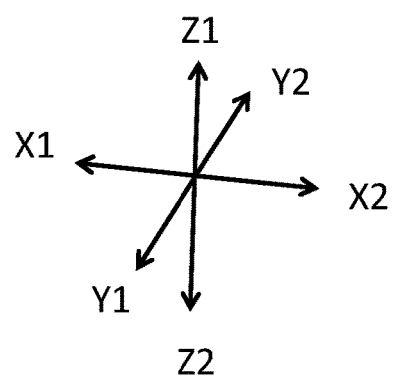

FIG. 7 is a schematic perspective view of the intraocular ring injector with a container 20 of this embodiment (a part of the hollow body 1 where the intraocular ring C and the pushing member 3 are present is illustrated as a transparent view), after moving the hollow body 1.

Next, only the hollow body 1 is moved forward. Since the flange 21 of the plunger 2 is fitted in the groove (i.e., the plunger movement restricting portion 5), the movement in the forward and backward direction is restricted. It means that the intraocular ring C having eyelet Ch engaging with the pushing member 3, and thus its protrusion 31, remains fixed, with the pushing member being connected to the plunger 2.

Thanks to the hollow body movement restricting portion 6, the hollow body 1 can be moved forward without the hollow body 1 being disengaged from the container 4. As a result, the intraocular ring C, which has been protruding out of the nozzle 12, can be stably and normally housed inside the hollow body 1 as illustrated in FIG. 7. Moreover, such housing can be done while the intraocular ring injector 10 is housed in container 4.

For example, in the case where the hollow body movement restricting portion 6 is an approximately C-shaped member, the operator may remove the hollow body 1 from the approximately C-shaped member to cancel the restrictions on the movement of the hollow body 1 by the hollow body movement restricting portion 6. However, it is preferred to employ a configuration of the hollow body movement restricting portion 6 where the restriction of the movement of the hollow body 1 is automatically canceled, when the hollow body 1 moves forward by the distance for housing the intraocular ring C in the hollow body 1, the intraocular ring C engaging with an axial end of the pushing member 3. It is because such a configuration can save operator's labor.

For example, the hollow body movement restricting portion 6 may be eliminated, when the hollow body 1 moves a distance such that the rest of the intraocular ring C excluding the vicinity of the eyelet Ch is housed in the hollow body 1.

Specifically, for example, the length in the forward and backward direction of the protrusion 1p provided on the outer circumference of the hollow body 1 and the length in the forward and backward direction of the protrusions 61 and 62 provided in the container 4 are set to the value equal to or close to that distance.

The same applies to the case where the hollow body movement restricting portion 6 is provided on the flange 11 of the hollow body 1. In such a case, for example, the length of the protrusions 61 and 62 provided in the container 4 is set to the value equal to or close to that distance.

The above-described distance may be set to, for example, 20 to 50 mm (preferably 25 to 45 mm) in consideration of the circumference of the known intraocular ring C.

By moving the hollow body 1 until the hollow body 1 hits the stopper 4s, the hollow body movement restricting portion 6 cancels the restriction on the movement of the hollow body 1. Then, the intraocular ring injector 10 can be taken out from the container 4 with the intraocular ring injector 10 facing upward (white arrow in FIG. 7).

In the case where the plunger movement restricting portion 5 is a groove and the plunger 2 (rod-shaped part, flange 21 of plunger 2) is fitted downward from above, the intraocular ring injector 10 can be easily taken out from the container 4 with the intraocular ring injector facing upward (white arrow in FIG. 7).

Otherwise, that is, even when the plunger movement restricting portion 5 is a ring-shaped member and fixes the plunger 2 itself, the intraocular ring injector 10 can be taken out from the container 4 with the intraocular ring injector facing upwards by separately releasing the fixation. However, the plunger movement restricting portion 5 that is a groove is more preferable because it does not require such a fixation-releasing operation.

It is preferred that the hollow body movement restricting portion 6 further has a return restricting portion 7 that restricts the hollow body 1 from moving rearward in the axial direction.

By way of a specific example, a leaf spring is provided on the left side or on the right side of the hollow body movement restricting portion 6 for the flange 21 of the plunger 2, the leaf spring having a length in an axial direction equivalent to the length of the second protrusion 62. This leaf spring is tapered so that the width in the vertical direction increases toward the front, for example. At the beginning of moving the hollow body 1 forward, the force pushing the hollow body 1 forward causes the hollow body 1 to move forward while the flange 11 of the hollow body pushes the leaf spring downward. Then, when the hollow body 1 is moved forward to the extent that the restriction of movement of the hollow body 1 is canceled, the flange 11 of the hollow body passes the tip end of the leaf spring, thereby eliminating the pressure on the leaf spring. As a result, the leaf spring is restored upwards and thus the flange 11 of the hollow body 1 cannot move rearward any longer.

In addition, the return restricting portion 7 having a configuration other than those described above may be adopted.

Figure 8A:
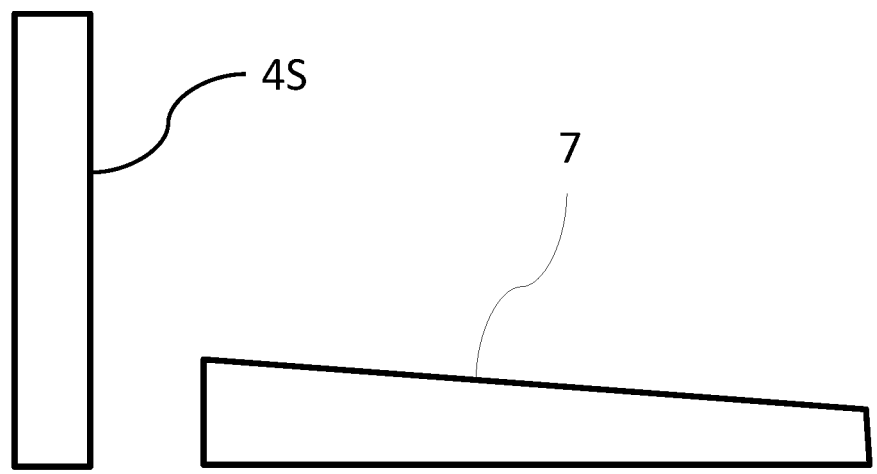
FIG. 8(*a*) is a schematic side view of an example of this embodiment in which a return restricting portion is distinct from a stopper, and FIG. 8(*b*) is a schematic side view of an example of modified embodiment in which a return restricting portion is integrated with a stopper.
Figure 8B:
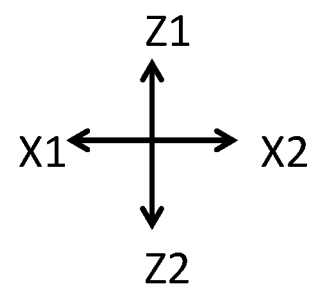

FIG. 8(a) is a schematic side view of an example of this embodiment in which a return restricting portion 7 is distinct from a stopper 4s, and FIG. 8(b) is a schematic side view of an example of modified embodiment in which a return restricting portion 7 is integrated with a stopper 4s.

Figure 8B:
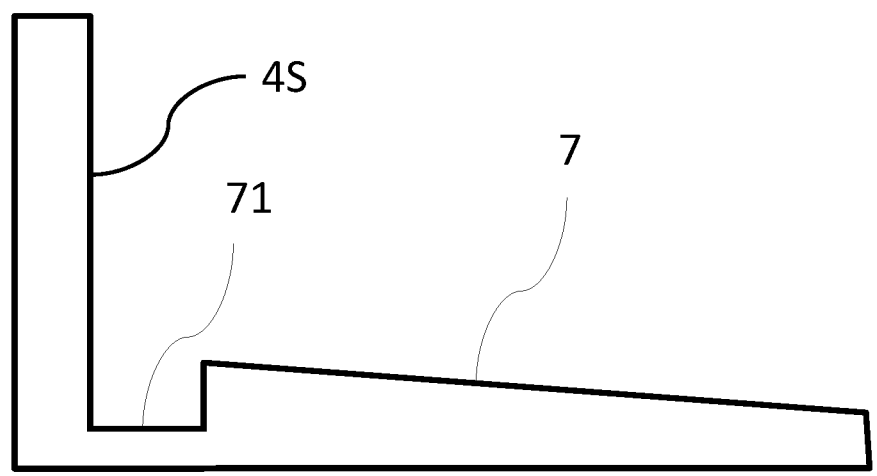

For example, as illustrated in FIG. 8 (b), the return restricting portion 7 and the stopper 4s may be integrated. In this case, the portion connecting the return restricting portion 7 to the stopper 4s forms groove 71. Therefore, as the hollow body 1 moves forward, the resistance increases. When the hollow body 1 moves forward to the extent that it contacts the stopper 4s, the cutout 11n of the flange 11 of the hollow body 1 engages with the groove 71, thereby fixing the hollow body 1 and restricting the hollow body 1 from returning rearward.

For example, in a configuration of the return restricting portion 7 other than those described above, one or more protrusions may be provided on the second protrusion 62, so that resistance is created when moving the hollow body 1 (and thus the flange 11 of the hollow body 1). This configuration can restrict the hollow body 1 from moving backward even when an unintended force is applied to the hollow body 1 that causes the hollow body 1 to move rearward.

FIG. 9 is a schematic side view of the nozzle 12 of the intraocular ring injector 10 of this embodiment.

It is also preferable that the shape of the nozzle 12 when viewed from the right-left direction (in a side view which is a direction perpendicular to the direction of releasing the intraocular ring C) is as follows. For example, the nozzle 12 may have a shape in which the upper part of the nozzle 12 has a long end 121 and the lower part of the nozzle 12 has the same or short end 122, and further the nozzle 12 may have a shape in which the same or short end 122 side of the opening 123 of the nozzle 12 is cut out (numeral reference, 123n).

By cutting out the opening 123 of the nozzle 12 as illustrated by the broken line in FIG. 9, the release direction of the intraocular ring C can be controlled.

More specifically, the intraocular ring C is first exposed to the outside of the opening 123 at the cutout portion 123n of the opening 123 of the nozzle 12. Since the intraocular ring C is curved, the intraocular ring C is easily discharged to the outside of the opening 123 while contacting the cutout portion 123n, as illustrated in FIG. 9.

In addition, the portion of the opening 123 pointed by the arrow 123n in FIG. 9 may be further cut out rearward. That is, an additional cutout may be provided rearward with respect to the cutout indicated by the broken line. The position of the additional cutout is preferably closer to the short end 122, compared to the midpoint between the upper long end 121 and the lower short end 122 of the nozzle 12.

The additional cutout can increase the area of the intraocular ring C contacting the opening during release of the intraocular ring C.

As a result, the intraocular ring C is easily released while the intraocular ring C is fitted in the cutout portion 123n. It means that the direction to which the intraocular ring C is released tends to be constant. Moreover, such tendency becomes remarkable by cutting out the short end 122 side of the opening 123 of the nozzle 12 when the nozzle 12 has a tapered shape in which the upper part of the nozzle 12 is long and the lower part is short.

Figure 10:
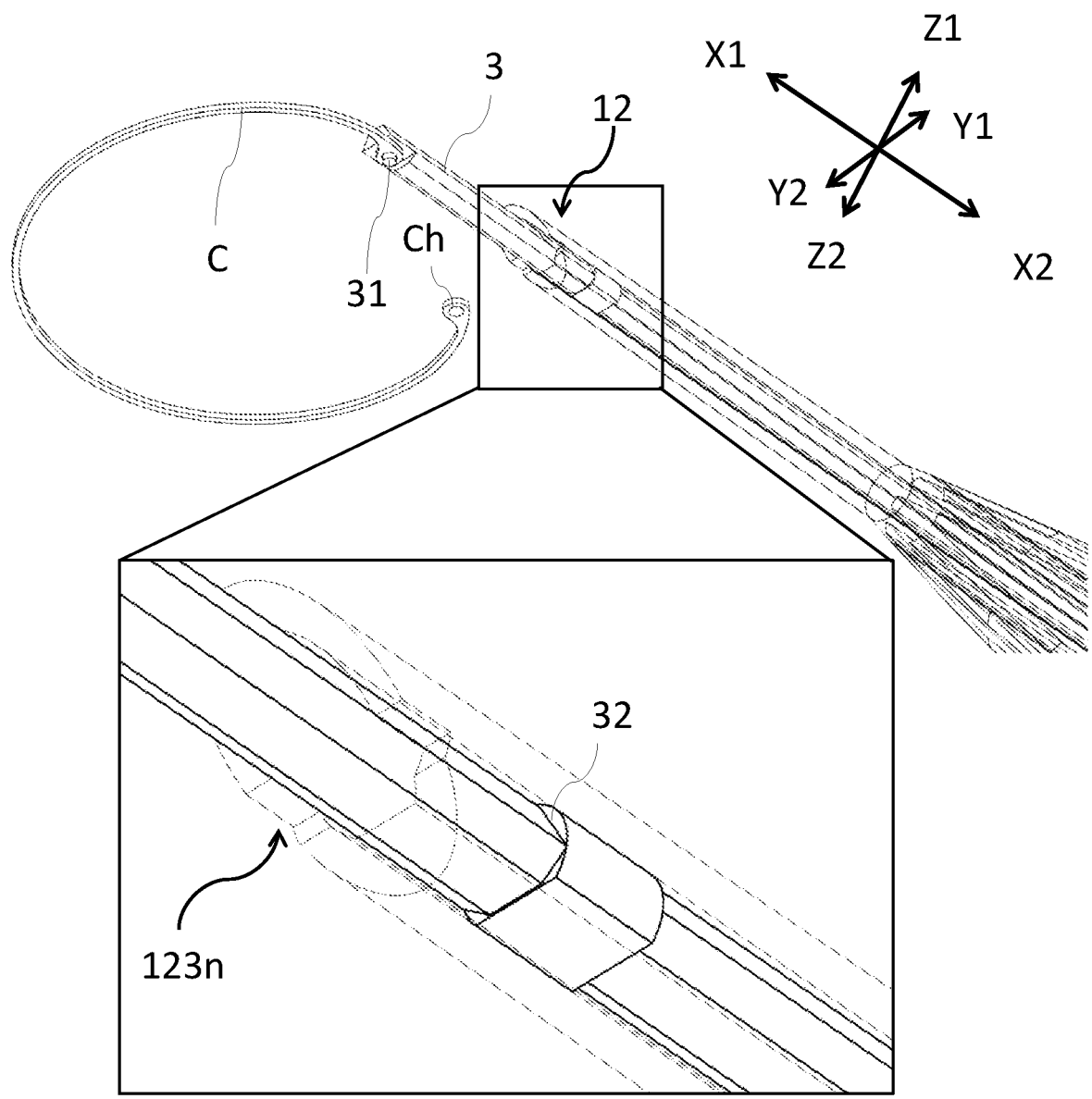
FIG. 10 is a schematic perspective view illustrating an overhanging portion provided in the pushing member of the intraocular ring injector of this embodiment.

FIG. 10 is a schematic perspective view illustrating overhanging portion 32 provided in the pushing member 3 of the intraocular ring injector 10 of this embodiment. Note that the nozzle 12 is illustrated as transparent.

As illustrated in FIG. 10, it is preferred to provide overhanging portion 32 in the pushing member 3 of the intraocular ring injector 10. This configuration can prevent the aqueous humor in the eye from flowing back into the nozzle 12 during the surgical procedure. The circumstances leading to the provision of this configuration will be hereinafter explained.

In the case of the intraocular ring injector 10 in which the intraocular ring C is housed in the nozzle 12, the intraocular ring C is not folded, unlike the intraocular lens. In the case of an intraocular "lens" injector, the intraocular lens is folded compactly and compressed, when it passes through the nozzle. Accordingly, there is almost no space through which the aqueous humor can flow back from the nozzle of the intraocular "lens" injector, so that the aqueous humor does not flow back.

Further, in a conventional intraocular ring injector, there is provided a gap (clearance) between a pushing member and an inner wall of a nozzle. That is, the present inventor has focused on the fact that the aqueous humor may possibly flow back into the nozzle during the surgical procedure in the conventional case. As a result, with the intention of preventing the backflow of the aqueous humor, the present inventor has devised a configuration in which at least a part of the pushing member 3 in the axial direction is provided with a flange, that is, overhanging portion 32, which overhangs in a direction perpendicular to the axial direction.

Examples of such a configuration include a configuration in which overhanging portion 32 for preventing backflow of the aqueous humor from the opening 123 of the nozzle 12 is provided only for a part of the pushing member 3 in the axial direction. Examples of such overhanging portion 32 include a flange which enables the pushing member 3 to have a diameter equal to the inner diameter of the nozzle 12. In other words, there may be a gap formed between the inner wall of the nozzle 12 and a portion in the axial direction other than the overhanging portion 32 of the pushing member 3, as in the conventional case. The gap is filled with the overhanging portion 32.

The overhanging portion 32 may be provided so that the pushing member 3 corresponds to the inner diameter of the nozzle 12. On the other hand, there may be a small gap between the pushing member and the inner wall of the nozzle 12, provided that backflow of the aqueous humor can be prevented.

The overhanging portion 32 may be provided on all the portions in the axial direction other than a part provided with the protrusion 31. However, as illustrated in FIG. 10, it may be provided on some of the portions, so as to reduce the weight of the pushing member 3, and thus the weight of the whole intraocular ring injector 10.

Further, a set of two plate-shaped protrusions 13a and 13b may be provided between the flange 11 on the outer circumference of the hollow body and the nozzle 12 in each of the right-left and up-down directions. With these plate-shaped protrusions 13a and 13b, an operator can easily grasp the orientation of the intraocular ring injector 10 when the operator grips the hollow body 1. Further, the plate-shaped protrusions 13a and 13b may be configured to become wider from the tip end toward the rear end. This makes it easier for the operator to grip the hollow body 1.

When viewed from the back to the front, the long end of the nozzle 12 is disposed at the position sandwiched between the upper set of two plate-shaped protrusions 13a and 13b. In other words, the opening 123 of the nozzle 12 is oriented forward and downward, and placed at the position between a lower set of two plate-shaped protrusions 13a and 13b. Thus, the operator can grasp the approximate position of the opening 123 of the nozzle 12 by reference to the upper set of two plate-shaped protrusions 13a and 13b.

Further, when viewed from the back to the front, another set of two plate-shaped protrusions 14a and 14b may be provided at the position sandwiched between the upper set of two plate-shaped protrusions 13a and 13b, and between the nozzle 12 and the plate-shaped protrusions 13a and 13b.

Figure 11A:
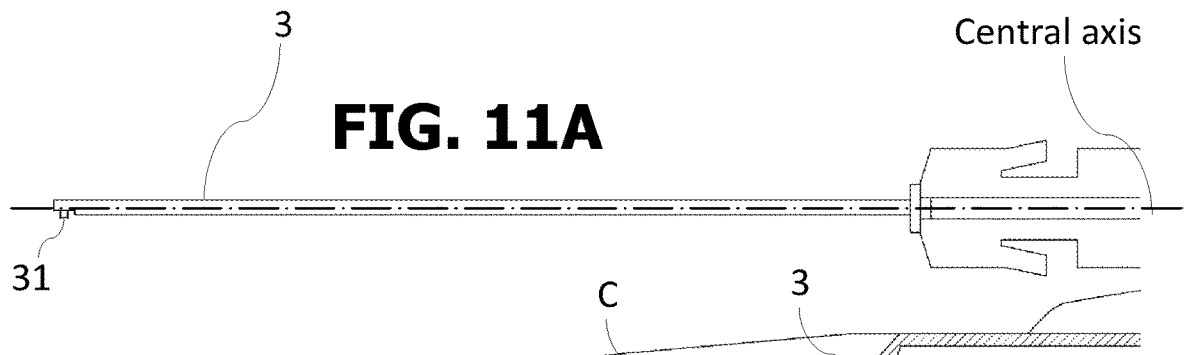
FIG. 11(*a*) is a schematic side view illustrating a pushing member of a conventional intraocular ring injector, and FIG. 11(*b*) is a schematic side view illustrating the vicinity of a nozzle of the conventional intraocular ring injector.
Figure 11B:
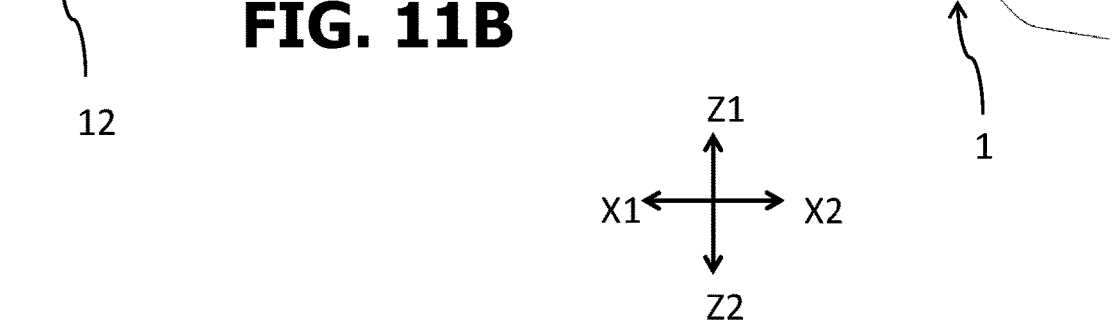

FIG. 11(a) is a schematic side view illustrating a pushing member of a conventional intraocular ring injector, and FIG. 11(b) is a schematic side view illustrating the vicinity of a nozzle of the conventional intraocular ring injector. Note that the nozzle is illustrated as transparent.

FIG. 12(a) is a schematic side view illustrating a pushing member 3 of the intraocular ring injector 10 of this embodiment, and FIG. 12(b) is a schematic side view illustrating the vicinity of a nozzle 12 of the intraocular ring injector 10 of this embodiment. Note that the nozzle 12 is illustrated as transparent.

As illustrated in FIG. 12, it is preferred to displace downward at least the tip end (front) part of the pushing member 3 of the intraocular ring injector 10 on the inner circumference of the nozzle 12, the tip end part having a protrusion 31 provided thereon. Focusing on the pushing member 3 alone, it is preferable to displace at least the above-described tip end part from the axial direction of the plunger 2 to the direction in which the protrusion 31 is protruded. This configuration can prevent the intraocular ring C from falling out of the protrusion 31 when pulling the intraocular ring C into the nozzle 12 and, in turn, making the intraocular ring C be housed in the hollow body 1. The circumstances leading to the provision of this configuration will be hereinafter explained.

The inner circumference of the nozzle 12 in this embodiment has a tapered shape with the thinner tip end side and the thicker rear end side. This embodiment is envisaged that this nozzle 12 is basically adopted, and the pushing member 3 and the plunger 2 are coaxially designed as illustrated in FIG. 11(a). In that case, as illustrated in FIG. 11(b), the more the intraocular ring C is pulled into the nozzle 12 and thus more into the hollow body 1 (hereinafter, description will be made for the nozzle 12), the larger the clearance (black arrow in FIG. 11(*b*)) between the protrusion 31 of the tip end part of the pushing member 3 and the inner circumference of the nozzle 12. As a result, while pulling the intraocular ring C into the inside of the nozzle 12, the intraocular ring C may be possibly disengaged from the protrusion 31 of the tip end part of the pushing member 3.

In this embodiment, as illustrated in FIG. 12(*a*), the tip end part of the pushing member 3 is designed to be located below the central axis of the plunger 2 (circled in FIG. 12(*a*)). In this configuration, as illustrated in FIG. 12(*b*), the clearance between the protrusion 31 of the tip end part of the pushing member 3 and the inner circumference of the nozzle 12 can be reduced (circled in FIG. 12(*b*)), the intraocular ring C being pulled into the inside of the nozzle 12. As a result, the intraocular ring C can be prevented from being disengaged from the protrusion 31 of the tip end part of the pushing member 3.

Specific aspects of the displacement are as follows.

For example, as illustrated in FIG. 12, the entire pushing member 3 attached to the plunger 2 or the entire rod-shaped part on the tip end side from the part engaged with the plunger 2 is tilted from the axial direction of the plunger 2 to the direction in which the protrusion 31 is protruded. Thereby, the tip end part of the pushing member 3 of the intraocular ring injector 10 can be displaced downward on the inner circumference of the nozzle 12, the tip end part having the protrusion 31 provided thereon. At this time, in the initial state where the protrusion 31 is fitted in the eyelet Ch of the intraocular ring C, the protrusion 31 may be displaced to the extent that it contacts the inner circumference of the nozzle 12. Further, the protrusion 31 may be displaced to the extent that it contacts the circumference of the nozzle 12 until it reaches the position where the intraocular ring C is pulled into the inside of the nozzle 12.

As another example, on the way from the rear end to the tip end of the pushing member 3, the pushing member 3 may be displaced in the direction in which the protrusion 31 is protruded, the pushing member 3 may extend as it is, and the tip end part provided with the protrusion 31 may be displaced downward on the inner circumference of the nozzle 12.

As still another example, only the tip end part of the pushing member 3 may be displaced downward on the inner circumference of the nozzle 12, the tip end part having the protrusion 31 provided thereon.

Each of the above configurations makes it possible to move forward the hollow body 1, which is a main body of the intraocular ring injector 10, while restricting the movement of the plunger 2 in the forward and backward direction in the state where the intraocular ring injector 10 is housed in the container 4. Thereby, the operation of making the intraocular ring C be housed in the intraocular ring injector 10 can be completed in the container 4.

In other words, the intraocular ring C can be stably housed in the hollow body 1 while stably maintaining the engagement between the pushing member 3 of the intraocular ring injector 10 and the eyelet Ch of the intraocular ring C. In addition, the operator can normally make the intraocular ring C be housed in the hollow body 1 while being conscious of the intraocular ring C and not being distracted by the movement of the plunger 2 as in the conventional case. In addition, since the operation is completed within the container 4, there is no risk of hitting the intraocular ring injector 10 against an obstacle outside the container 4 during the operation of making the intraocular ring C be in housed.

As a result, the operator can make the intraocular ring C be stably and normally housed in the intraocular ring injector 10.

The technical scope of the present invention is not limited to the embodiments described above but includes various modes and modifications as far as the specific effects obtained by the constituent features of the invention and combinations thereof can be derived.

For example, the intraocular ring injector 10 of this embodiment may be, for example, a disposable type made of resin, or it may be a repeatedly usable type. However, the disposable type is preferable because it does not need to be cleaned and disinfected each time, which saves time and labor.

This embodiment has been illustrated mainly referring to an example in which the movement of the plunger 2 in the axial direction is mainly restricted, while the hollow body 1 is allowed to move only in the axial direction. However, the above relationship may be reversed. For example, the movement of the hollow body 1 in the axial direction is restricted, while the movement of plunger 2 is allowed only in the axial direction. The "moving mechanism of moving the hollow body 1 and the plunger 2 relatively in the axial direction, while housing the intraocular ring injector 10 in the container 4" described previously in this embodiment includes this configuration.

In this modified example, similar to this embodiment, it is preferable to have a sliding mechanism capable of sliding at least one of the hollow body 1 and the plunger 2 in the axial direction while housing the intraocular ring injector 10 in the container 4. Then, it is more preferred to have a movement restricting portion that restricts the movement of the intraocular ring injector 10 while being housed in the container 4 in a direction other than the axial direction.

In this modified example, it is preferable that the movement restricting portion cancels restriction on the movement of the intraocular ring injector 10, when the hollow body 1 and the plunger 2 are relatively moved, that is, the hollow body 1 is fixed and then the plunger 2 is moved by a distance for housing the intraocular ring C in the hollow body 1, the intraocular ring being engaged with an axial end of the pushing member.

As a specific configuration, for example, a vertical groove into which the flange 11 of the hollow body 1 can be fitted downward from above may be provided in the container 4. Then, an engagement mechanism similar to the protrusion 1*p* of the hollow body 1 and the first protrusion 61 of the container may be provided in the rod-shaped portion of the plunger 2 and in the container 4. Alternatively, an engagement mechanism similar to the cutout 11*n* of the flange 11 of the hollow body 1 and the second protrusion 62 of the container may be provided for the flange 21 of the plunger 2.

Alternatively, the hollow body 1 and the plunger 2 may be moved together. In this case, an engagement mechanism similar to the protrusion 1*p* of the hollow body 1 and the first protrusion 61 of the container, or an engagement mechanism similar to the cutout 11*n* of the flange 11 of the hollow body 1 and the second protrusion 62 of the container may be provided for the plunger 2, the hollow body 1, and the container 4.

In any case, the moving distance is preferably 20 to 50 mm (preferably 25 to 45 mm), as in this embodiment.

In this embodiment, the lens capsule tension ring (CTR) is exemplified as the intraocular ring C. On the other hand, the technical idea of the present invention can also be applied to the intraocular ring injector 10 which utilizes the intracorneal ring as the intraocular ring C.

Further, the above embodiment in which the nozzle 12 is cut out can be an invention by itself, by setting the release direction of the intraocular ring C tending to be constant as the problem and effect of the invention. Moreover, the problem and effect can be applied not only to the intraocular ring C but also to the intraocular lens. In view of the foregoing, one configuration of the present invention is as follows.

"An injector for injecting an intraocular ring C for retaining a shape of a lens capsule, or an intraocular lens into an eye, including nozzle 12 for releasing the intraocular ring C or intraocular lens, wherein the nozzle 12 has a shape in which one end 121 is long and the other end 122 is the same or short, and the same or short one end 122 side of the opening 123 of the nozzle 12 is cut out, in a side view which is a direction perpendicular to the releasing direction".

Preferably, with respect to a cutout on the same or short end 122 side, an additional cutout is provided rearward at the position closer to the short end 122 relative to a midpoint between an upper long end 121 and a lower short end 122 of the nozzle 12.

The overhanging portion 32 provided in the pushing member 3 described above can be an invention by itself, by setting the prevention of the backflow of the aqueous humor as the problem and effect. In view of the foregoing, one configuration of the present invention is as follows.

"An intraocular ring injector 10 for injecting an intraocular ring C into an eye for retaining a shape of a lens capsule, the intraocular lens injector 10 including:
hollow body 1 having a hollow part in which the intraocular ring C is housed;
plunger 2 that moves through an inside of the hollow body 1 in an axial direction of the hollow body; and
pushing member 3 that pushes out the intraocular ring C by moving forward together with the plunger 2 through the inside of the hollow body 1 in the axial direction of the hollow body 1,
wherein the hollow body 1 includes the nozzle 12 releasing the intraocular ring C through the opening 123, and overhanging portion 32 is provided to at least a part of the pushing member 3 in the axial direction, for preventing backflow of the aqueous humor from the opening 123 of the nozzle 12".

The above-described displacement of the pushing member 3 can be an invention by itself, by setting the intraocular ring C being possibly disengaged from the protrusion 31 of the tip end part of the pushing member 3 while pulling the intraocular ring C into the inside of the nozzle 12, as a problem and to solve the above problem is envisaged as an effect. In view of the foregoing, one configuration of the present invention is as follows.

"An intraocular ring injector 10 for injecting an intraocular ring C into an eye for retaining a shape of a lens capsule, the intraocular lens injector 10 including:
hollow body 1 having a hollow part in which the intraocular ring C is housed;
plunger 2 that moves through an inside of the hollow body 1 in an axial direction of the hollow body; and
pushing member 3 that pushes out the intraocular ring C by moving forward together with the plunger 2 through the inside of the hollow body 1 in the axial direction of the hollow body 1,
wherein at least a front portion of the pushing member 3 on which a protrusion 31 for engagement with the intraocular ring C is provided, is displaced from the axial direction of the plunger 2 to a direction in which the protrusion 31 is protruded".

DESCRIPTION OF SIGNS AND NUMERALS

1 Hollow body
1p Protrusion (for groove formation)
11 Flange of hollow body
11n Cutout (of flange of hollow body)
12 Nozzle
121 Long end
122 Same or short end
123 Opening of nozzle
123n Cutout (of opening of nozzle)
13a, 13b Plate-shaped protrusion
14a, 14b Another plate-shaped protrusion
2 Plunger
21 Flange of plunger
3 Pushing member
31 Protrusion (for eyelet)
32 Overhanging portion (for preventing backflow of aqueous humor)
4 Container
4s Stopper
5 Plunger movement restricting portion
6 Hollow body movement restricting portion
61, 62 First protrusion, second protrusion (as hollow body movement restricting portion)
7 Return restricting portion
71 Groove (engaging with cutout of flange of hollow body)
8 Lid
9 Hook
10 Intraocular ring injector
20 Intraocular ring injector with container
C Intraocular ring
Ch Eyelet

What is claimed is:

1. An intraocular ring injector system for use with an intraocular ring, comprising:
   an intraocular ring injector including
      a hollow body having a nozzle and an inside defining an axial direction and a hollow part configured to house the intraocular ring,
      a plunger that moves through the inside of the hollow body in the axial direction,
      a pushing member, operably connected to the plunger, that moves with the plunger to push the intraocular ring in the axial direction and through the nozzle;
   a container configured to house the intraocular ring injector in such a manner that the nozzle is located within the container; and
   a movement control mechanism, associated with the container, configured to allow at least one of the hollow body and the plunger to move in the axial direction relative to the other of the hollow body and the plunger, and to prevent movement of the hollow body and the plunger in directions other than the axial direction, while housing the intraocular ring injector in the container;
   wherein the intraocular ring injector and the container are respectively configured such that the entire intraocular ring injector can be removed from the container.

2. The intraocular ring injector system according to claim 1, wherein the movement control mechanism cancels restriction of the movement of the intraocular ring injector when the hollow body and the plunger are moved relative to one another by a distance sufficient to house an intraocular ring in the hollow body, and the pushing member includes an axial end that is configured to engage an intraocular ring.

3. The intraocular ring injector system according to claim 1, wherein the movement control mechanism comprises:
a plunger movement restricting portion that restricts movement of the plunger in the axial direction while the intraocular ring injector is housed in the container; and
a hollow body movement restricting portion that restricts movement of the hollow body in a direction other than the axial direction, and permits movement of the hollow body in the axial direction, while the intraocular ring injector is housed in the container.

4. The intraocular ring injector system according to claim 3, wherein the hollow body movement restricting portion cancels the restriction of the movement of the hollow body when the hollow body moves forward by a distance sufficient to house an intraocular ring in the hollow body.

5. The intraocular ring injector system according to claim 3, wherein the hollow body movement restricting portion comprises a plurality of hollow body movement restricting portions.

6. The intraocular ring injector system according to claim 3, wherein
the hollow body defines an outer surface, and
the hollow body movement restricting portion is configured to engage the outer circumference of the hollow body in the axial direction.

7. The intraocular ring injector system according to claim 3, wherein the hollow body movement restricting portion includes a return restricting portion that restricts the hollow body from moving rearward in the axial direction.

8. The intraocular ring injector system according to claim 3, wherein
the plunger includes a rear end, and
the plunger movement restricting portion comprises a groove that engages the rear end of the plunger in the axial direction.

9. The intraocular ring injector system according to claim 1, wherein
the nozzle has an opening for releasing an intraocular ring, and
the nozzle has a shape with a long end and a short end, and a short end side of the nozzle opening is cut out in a side view which is in a direction perpendicular to the axial direction of the hollow body, or
the nozzle has a shape with two ends that are the same.

10. The intraocular ring injector system according to claim 1, wherein
the nozzle has an opening for releasing an intraocular ring, and
the pushing member has an overhanging portion for preventing backflow of an aqueous humor from the nozzle opening.

11. The intraocular ring injector system according to claim 1, wherein
the pushing member includes a front portion with a protrusion that displaces the plunger from the axial direction.

12. The intraocular ring injector system according to claim 1, further comprising:
an intraocular ring.

13. An intraocular ring injector system for use with an intraocular ring, comprising:
an intraocular ring injector including
a hollow body having a nozzle and an inside defining an axial direction and a hollow part configured to house the intraocular ring,
a plunger that moves through the inside of the hollow body in the axial direction,
a pushing member, operably connected to the plunger, that moves with the plunger to push the intraocular ring in the axial direction toward the nozzle;
a container configured to house the intraocular ring injector; and
a movement control, associated with the container, configured to allow at least one of the hollow body and the plunger to move in the axial direction relative to the other of the hollow body and the plunger, and to prevent movement of the hollow body and the plunger in directions other than the axial direction, while housing the intraocular ring injector in the container, wherein
the movement control mechanism cancels restriction of the movement of the intraocular ring injector when the hollow body and the plunger are moved relative to one another by 20 to 50 mm, and
the pushing member includes an axial end that is configured to engage an intraocular ring.

14. An intraocular ring system, comprising:
a container;
an intraocular ring injector housed in the container and including
a hollow body defining an axial direction and a tip end,
a nozzle at the tip end of the hollow body and located within the container,
a plunger that moves through the hollow body in the axial direction,
a pushing member, including a distal end configured to engage an intraocular ring, operably connected to and movable with the plunger in the axial direction and through the nozzle;
a movement control mechanism, associated with the container, configured to allow at least one of the hollow body and the plunger to move in the axial direction relative to the other of the hollow body and the plunger while the intraocular ring injector is housed in the container; and
an intraocular ring, configured to retain a lens capsule shape, located within the container and engaged with the distal end of the pushing member.

15. The intraocular ring system according to claim 14, wherein
the intraocular ring injector is further configured to prevent movement of the hollow body and the plunger in directions other than the axial direction while the intraocular ring injector is housed in the container.

16. The intraocular ring system according to claim 14, wherein
the movement control mechanism comprises
a plunger movement restricting portion that restricts movement of the plunger in the axial direction while the intraocular ring injector is housed in the container; and
a hollow body movement restricting portion that restricts movement of the hollow body in a direction other than the axial direction, and permits movement of the hollow body in the axial direction, while the intraocular ring injector is housed in the container.

17. The intraocular ring system according to claim 14, wherein
> the movement control mechanism is configured to cancel restriction of the movement of the intraocular ring injector after the hollow body and the plunger have been moved relative to one another by a distance sufficient to pull the intraocular ring into the nozzle.

18. The intraocular ring system according to claim 14, wherein
> the intraocular ring comprises an arc-shaped wire.

19. The intraocular ring system according to claim 18, wherein
> the pushing member includes a protrusion; and
> the intraocular ring includes an eyelet configured to receive the protrusion.

* * * * *